United States Patent [19]
Salansky et al.

[11] Patent Number: 6,063,108
[45] Date of Patent: *May 16, 2000

[54] METHOD AND APPARATUS FOR LOCALIZED LOW ENERGY PHOTON THERAPY (LEPT)

[76] Inventors: Norman Salansky; Natalia Filonenko, both of 131 Torresdale Avenue, Apartment 1106, North York, Canada, M2R 3T1

[ * ] Notice: This patent issued on a continued prosecution application filed under 37 CFR 1.53(d), and is subject to the twenty year patent term provisions of 35 U.S.C. 154(a)(2).

[21] Appl. No.: 08/779,316

[22] Filed: Jan. 6, 1997

[51] Int. Cl.[7] ................................................ A61N 5/06
[52] U.S. Cl. .............................. 607/89; 606/9; 606/13
[58] Field of Search .......................... 607/88, 89, 90, 607/91, 92; 606/2, 9, 10, 13–17

[56] References Cited

U.S. PATENT DOCUMENTS

| | | |
|---|---|---|
| 4,440,160 | 4/1984 | Fischell et al. .......................... 128/857 |
| 4,669,466 | 6/1987 | L'Esperance ................................. 606/3 |
| 4,930,504 | 6/1990 | Diamantopoulos ........................ 607/88 |
| 5,312,396 | 5/1994 | Feld et al. .................................. 606/11 |
| 5,549,660 | 8/1996 | Mendes et al. ............................ 607/88 |
| 5,638,593 | 6/1997 | Gerhardt et al. ........................ 29/592.1 |
| 5,674,217 | 10/1997 | Wahlstrom et al. ....................... 606/16 |
| 5,735,285 | 4/1998 | Albert et al. ............................. 128/904 |

*Primary Examiner*—Michael Peffley
*Assistant Examiner*—Rosiland Kearney
*Attorney, Agent, or Firm*—Bereskin & Parr

[57] ABSTRACT

An apparatus for treating a disorder of a biological tissue in a mammal by stimulating the biological tissue with light having selected optical parameters. The apparatus has a power source, a central microprocessor with stored optical parameter protocols and wireless probes to receive the protocols and to generate and transmit the light. The invention also relates to a method for stimulating healing of a disorder of a biological tissue in a mammal by stimulating the biological tissue with light having selected optical parameters.

26 Claims, 17 Drawing Sheets

RESULTS OF MONTE-CARLO SIMULATION OF
PHOTON PROPOGATION IN THE SKIN.
BEAM : FLAT, R = 1 cm.

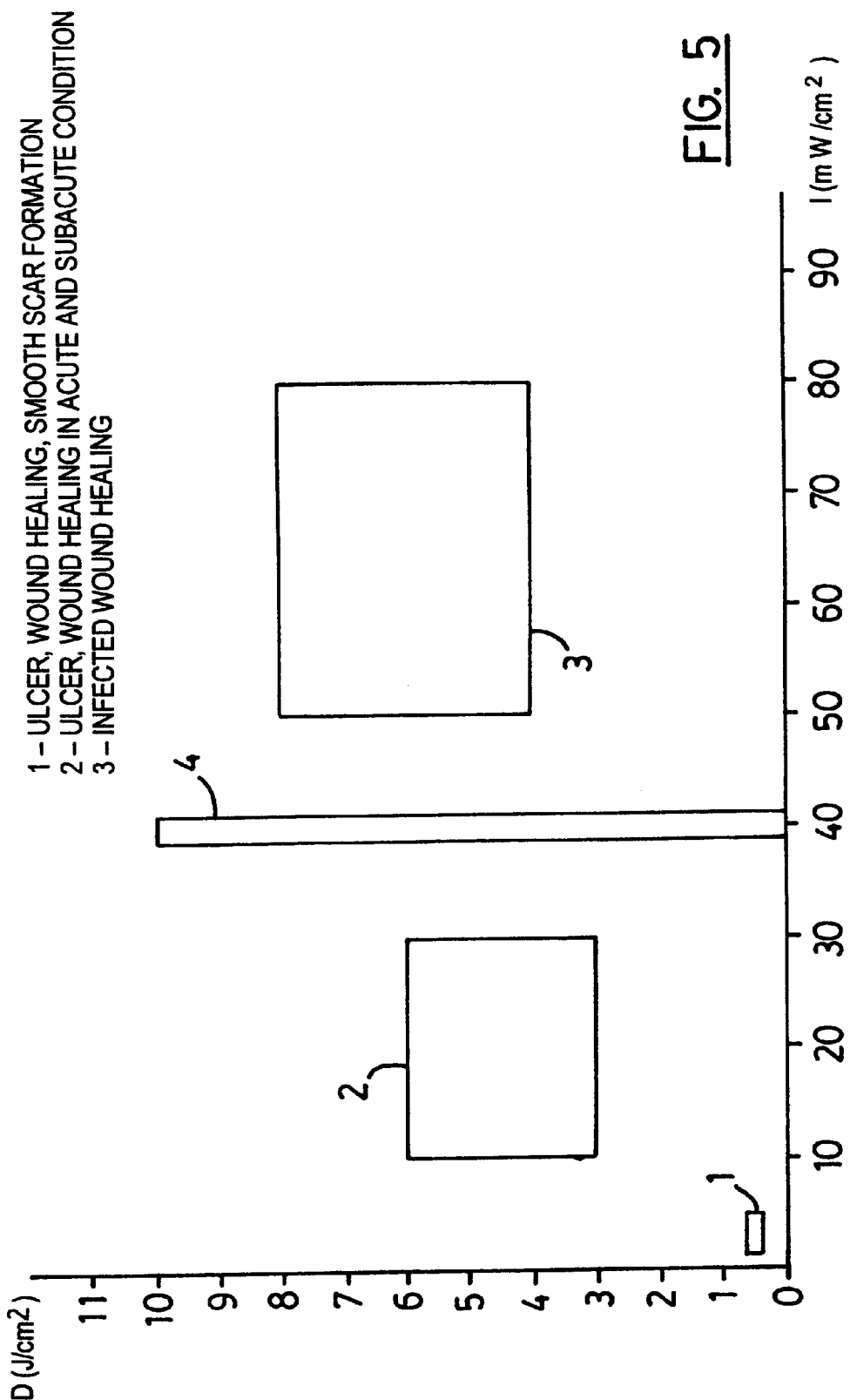

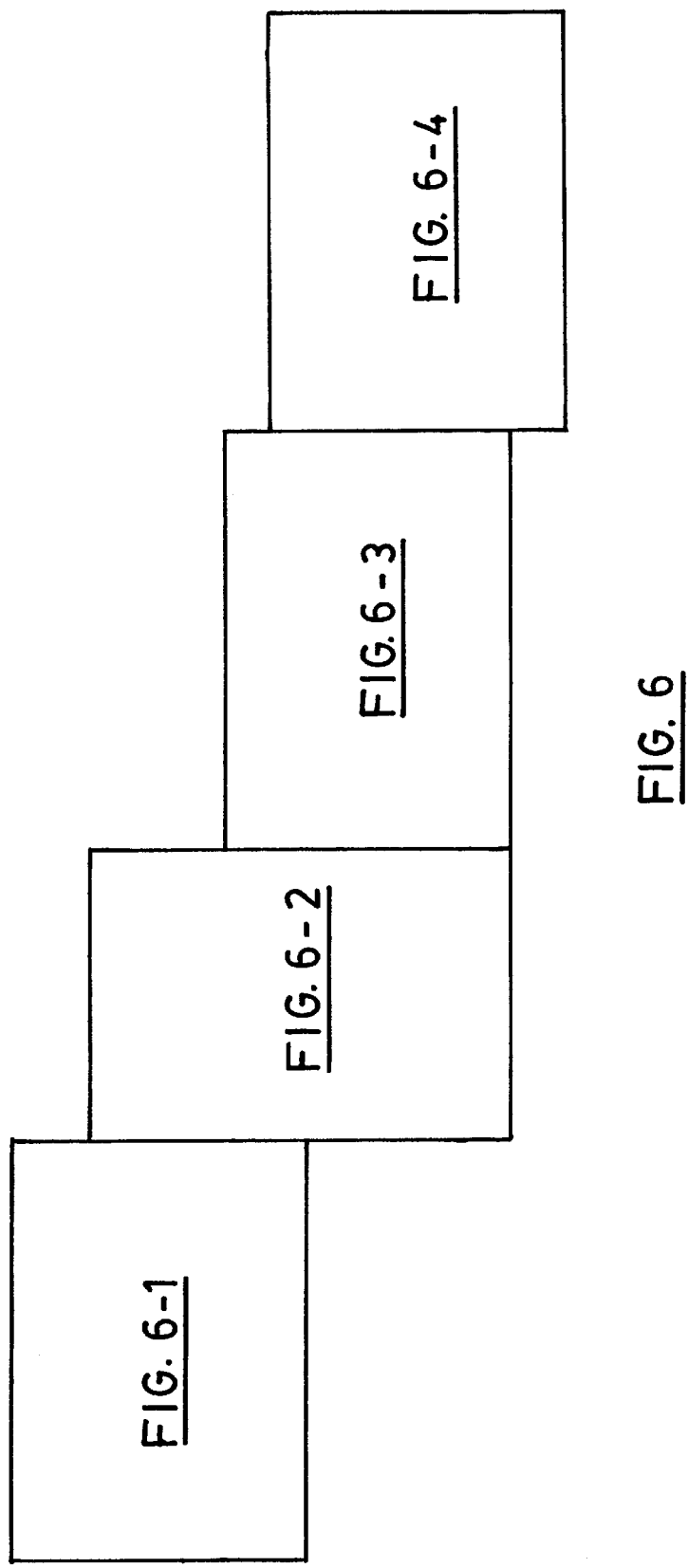

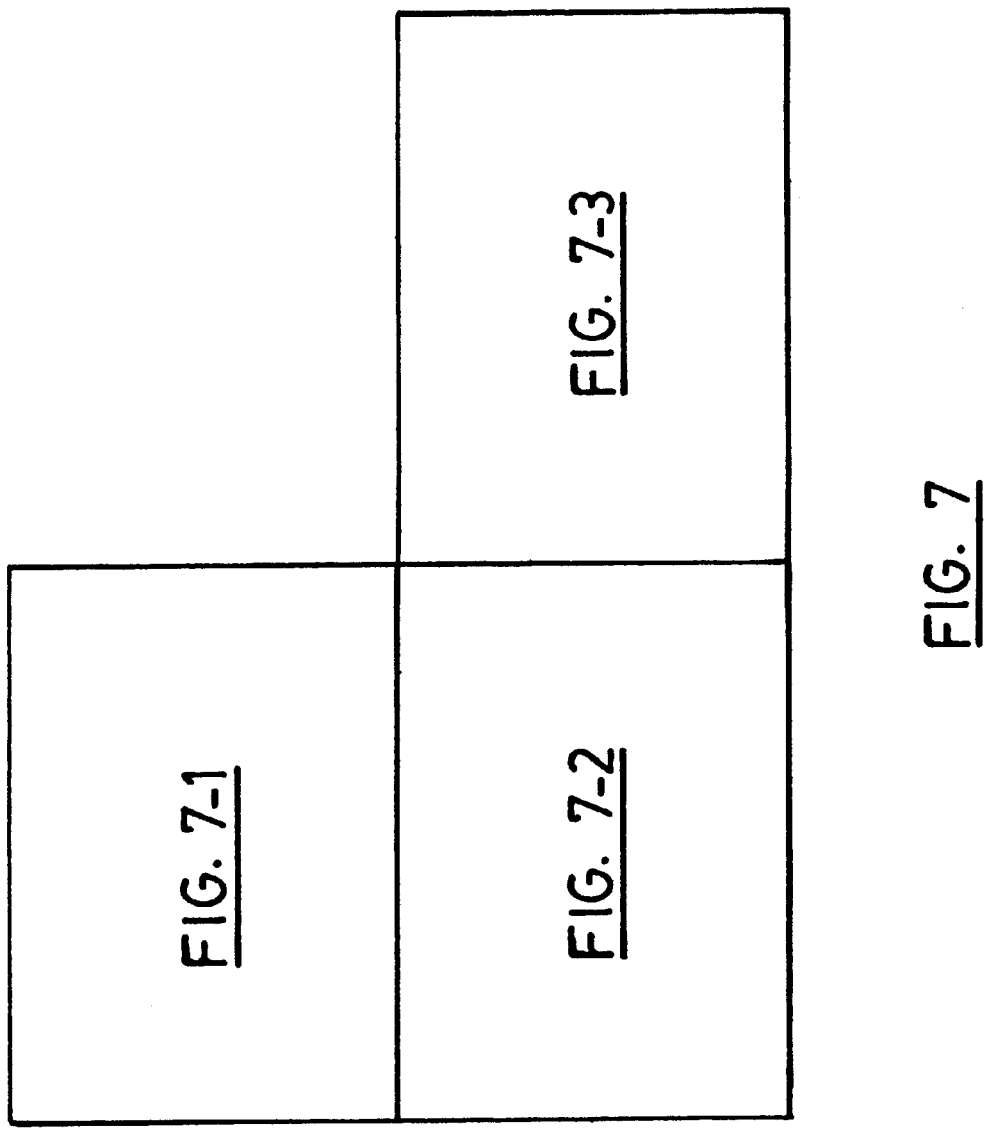

LEGEND: ○ OFF
⊘ ON

METHOD AND APPARATUS FOR LOCALIZED LOW ENERGY PHOTON THERAPY (LEPT)

FIELD OF THE INVENTION

The invention relates to an apparatus for treating disorders of biological tissues with light of selected optical parameters. The invention also relates to methods for stimulating healing of disorders of biological tissue with light having selected optical parameters and to methods of stimulating healing of lesions using such light.

BACKGROUND OF THE INVENTION

Curing with light was known and used in medicine in ancient times. Red or ultraviolet light was successfully used in the 19th century for the treatment of pockmarks and lupus vulgaris by Danish physician, N. R. Finsen, the father of contemporary phototherapy.

Biological phenomena induced by ultraviolet light have been intensively investigated in photobiology and photomedicine for several decades. Ultraviolet light as a phototherapy for some dermatological diseases (mainly psoriasis) has been used since the early twenties. However, ultraviolet light is an ionizing radiation, and therefore has a damaging potential for biomolecules and has to be used in photomedicine with certain precautions.

Biological and healing phenomena induced by optical wavelength (visible) and infrared (invisible) light have been intensively investigated in the last decade. Electromagnetic waves with optical (visible light) and near infrared (invisible irradiation) wavelengths ($\lambda$=400–2,000 nm) provide non-ionizing radiation and have been used in vivo, in vitro and in clinical studies, as such radiation does not induce mutagenic or carcinogenic effects.

Lasers, specific light sources which provide narrow-band monochromatic, coherent, polarized light with wide range of powers and intensities, have been widely used in medicine. Medical lasers may be subdivided into three groups according to their power and ability to produce heat: hot lasers, which are used in surgery; mid power lasers which are used in photodynamic therapy for cancer treatment or in dermatology to treat telangiectasia, port-wine stains, etc.; and low energy (or low intensity, cold or low level) lasers which deliver several orders of magnitude less energy to the tissue than surgical lasers. They produce very little heat in biological tissue or no heat at all.

Low energy lasers have been used in dermatology, traumatology and some other areas to enhance healing phenomena in the body (Mester et al., *Lasers Surg. Med.* 5:31–39, 1985; Trelles et al., *Lasers Surg. Med.* 7:36–45, 1987; Ohshiro T., *Laser Therapy: Practical Applications,* (Ed. T. Ohshiro), John Wiley, Chichester, 1991). The most frequently used terms for this area of physiotherapy are low Energy Laser Therapy (LELT), Low reactive Level Laser Therapy (LLLT), or Laser Therapy. The first successes of LELT were demonstrated in the treatment of chronic ulcers and persistent wounds of different etiology (Mester et al., *Lasers Surg. Med.* 5:31–39, 1985).

Anecdotal case studies have suggested that LELT is beneficial for a number of dermatological and musculoskeletal conditions. However, LELT has failed to provide good results in well-controlled randomized double-blind studies designed in accordance with rigorous North-American standards (Gogia and Marquez, *Ostomy/Wound Management,* 38:38–41, 1992; Lundeberg and Malm, *Ann. Plast. Surg.,* 27:53).

Coherence and polarization are the main features which differentiate laser light from regular monochromatic light. Many photoinduced phenomena in cell cultures and biotissue are reported to be induced by noncoherent, nonpolarized monochromatic light (Karu, *Health Physics,* 56:691–704, 1989 and Karu, *IEEE J. of Quantum Electronics,* QE23:1703–1717, 1987).

Laser beams lose coherence and polarization because of scattering very quickly after entering tissue and thus deeper tissue layers "do not distinguish" laser from non-laser light.

Low energy photon therapy (LEPT), also known as low energy, low level, low intensity laser therapy, photobiomodulation, is the area of photomedicine where the ability of monochromatic light to alter cellular function and enhance healing non-destructively is a basis for the treatment of dermatological, musculosketal, soft tissue and neurological conditions.

Low energy photons with wavelengths in the range of 400 nm–2,000 nm have energies much less than ultraviolet photons, and therefore, low energy photons do not have damaging potential for biomolecules as ionizing radiation photons have.

The area of LEPT research is controversial and has produced very variable results, especially in clinical studies. Almost every mammalian cell may be photosensitive, e.g. could respond to monochromatic light irradiation by changes in metabolism, reproduction rate or functional activity. Monochromatic light photons are thought to be absorbed by some biological molecules, primary photoacceptors, presumably enzymes, which change their biochemical activity. If enough molecules are affected by photons, this may trigger (accelerate) a complex cascade of chemical reactions to cause changes in cell metabolism. Light photons may just be a trigger for cellular metabolism regulation. This explains why low energies are adequate for these so called "photobiomodulation") phenomena. However, it is difficult to induce and observe these phenomena both in vivo and in vitro using the same optical parameters. Specific optical parameters are required to induce different photobiomodulation phenomena (Karu, *Health Physics,* 56:691–704, 1989; Karu, *IEEE J. of Quantum Electronics,* QE23:1703–1717, 1987). The range of optical parameters where "photobiomodulation" phenomena are observed may be quite narrow. The specificity and narrowness of the optical parameters required for "photobiostimulation" in LEPT therapy distinguishes LEPT therapy from the photodestruction phenomena induced by hot and mid power lasers (e.g. in surgery and PDT).

Devices for stimulating biological tissue using low energy light are disclosed for example in U.S. Pat. No. 4,930,504 to Diamantopoulos et al. and U.S. Pat. No. 4,686,986 to Fenyo et al., U.S. Pat. No 4,535,784 to Rohlicek describes an apparatus for stimulating acupuncture points using light radiation. U.S. Pat. No. 4,672,969 to Dew describes a method and apparatus for closing wounds using a laser tuned to a wavelength of 1.33 $\mu$m to produce thermal heating of the tissue to denature the protein.

To meet the changing requirements for optical parameters for different experimental and clinical applications, there is a need for an optical system for "photobiomodulation" having flexible parameters, adjustable for particular applications. In particular, there is a need for an apparatus capable of treating a range of biological disorders by reliably providing light to the affected three dimensional biological tissue, which light has the optical parameters necessary for inducing the appropriate photobiomodulation for the particular disorder and tissue to be treated. There is also a need for a method for reliably providing light having such parameters to a biological tissue having a disorder in order to effect healing.

SUMMARY OF THE INVENTION

The present inventors have determined that for each disorder of biological tissue there is a set of optical parameters which constitute the optimal protocol for treating the disorder by LEPT. The optimal protocol depends on a range of factors such as the type of tissue affected, the disorder, the stage of tissue healing (acute, subacute, tissue regeneration stage) and the size and three dimensional placement of the affected area. The optical parameters which make up the protocol include optical power, dose, intensity, wavelength, bandwidth, beam diameter and divergence, frequency and pulse duration. The present inventors have also determined that these protocols may be developed, stored, selected, retrieved from a microprocessor and utilized to provide optimal LEPT treatment for a range of biological disorders efficiently and reliably.

The present invention thus provides an apparatus for treating a disorder of a biological tissue in a mammal by stimulating the biological tissue with light having selected optical parameters. The apparatus comprises a power source for providing power to a central microprocessor; a central microprocessor having stored optical parameter protocols suitable for treating a range of disorders of biological tissue and means for selecting one or more stored optical parameter protocols for the disorder to be treated; including at least one wireless optical probe, having a microprocessor in communication with the central microprocessor, to receive the selected optical parameter protocol and having at least one probe containing an optical source(s) for generating a beam(s) of light having the selected optical parameter protocol and for directing the beam of light to the biological tissue to be treated; and communication means for transmitting the optical parameter protocol from the central microprocessor to the probes, or remotely via telephone and satellite links to any location around the world or outer space.

In an embodiment, the beam of light having the selected optical parameter protocol is substantially monochromatic and has a wavelength of from 400 to 2,000 nm and preferably has a wavelength in the range of from 500 to 2,000 nm, more preferably from 600 to 1,100 nm. In particular, embodiments, preferred ranges include from 360 to 440 nm, from 630 to 700 nm, from 740–760 nm, or from 800–1,100 nm. The optical source may be, for example a laser, laser diode, superluminous or light emitting diode. In an embodiment, the optical source is in pulsed mode with an operating frequency in a range of from 0 to 200 Hz and 1,000–10,000 Hz for short pulses. In a further embodiment, the optical parameters are optical power, dose and intensity, frequency, modulation frequency and phase of stimulation.

The wireless communication means may be acoustic, magnetic or optical.

In a still further embodiment, the apparatus further comprises means for monitoring the condition of the mammal and providing feedback to the central microprocessor to adjust the selected optical parameter protocol based on the condition of the mammal. The means for monitoring the condition of the mammal may be for example EEG (electroencefalography), EMG (electromyography), ECG (electrocardiography), CL (chemoluminescence) or a respirator, or a combination thereof.

In a further embodiment the apparatus comprised and utilized means to modulate treatment optical parameters by endogenous (such as respiratory, ECG, EEG, etc.) frequencies and to provide on-line feedback for selection of stimulation phase in respect to any endogenous rhythm phases.

Another aspect of the invention relates to a method for stimulating healing of a disorder of a biological tissue in a mammal by stimulating the biological tissue with light having selected optical parameters provided by a central microprocessor having stored optical parameter protocols suitable for treating a range of disorders of biological tissue; selecting one or more stored optical parameter protocols for the disorder to be treated; generating a beam of light having the selected optical parameter protocol and directing the beam of light to the biological tissue to be treated.

In an embodiment, the invention provides a method of stimulating healing of a lesion in a mammal, comprising: irradiating the lesion with a substantially monochromatic beam of light having predetermined optical parameters, wherein the predetermined optical parameters include a dose of from 0.2 to 10 J/cm$^2$, an intensity of from 0.2 to 5,000 mW/cm$^2$ and a wavelength of from 400 to 2,000 nm.

In a particular embodiment of the method, the lesion is a chronic ulcer or wound and the selected optical parameters include a dose of from 0.2 to 1.0 J/cm$^2$, an intensity of from 0.2 to 10 mW/cm$^2$ and a wavelength of from 600 to 700 nm. In another embodiment of the method, the lesion is an acute ulcer or wound and the selected optical parameters include a dose of from 2.0 to 5.0 J/cm$^2$, an intensity of from 10.0 to 30 mW/cm$^2$ and a wavelength of from 600 to 700 nm. In yet another embodiment, the lesion is an infected wound and the selected optical parameters include a dose of from 3.0 to 7.0 J/cm$^2$, an intensity of from 50.0 to 80 mW/cm$^2$ and a wavelength of from 600 to 700 nm.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 5 shows a simplified two-dimensional diagram of desired parameters for low energy photon therapy for a particular condition and an example of the range produced by a typical given laser;

DETAILED DESCRIPTION OF PREFERRED EMBODIMENTS

As hereinbefore mentioned, the present invention provides an apparatus for treating a disorder of a biological tissue in a mammal by stimulating the biological tissue with light having selected optical parameters. The apparatus comprises a power source for providing power to a central microprocessor; a central microprocessor having stored optical parameter protocols suitable for treating a range of disorders of biological tissue and means for selecting one or more stored optical parameter protocols for the disorder to be treated; at least one wireless probe, having a microprocessor in communication with the central microprocessor, to receive the selected optical parameter protocol and having at least one probe containing an optical source for generating a beam of light having the selected optical parameter protocol and for directing the beam of light to the biological tissue to be treated; and wireless communication means for transmitting the optical parameter protocol from the central microprocessor to the wireless heads.

A wide range of disorders of biological tissue or their symptoms may be treated by the apparatus of the invention, including acute and chronic musculoskeletal conditions, such as arthritis, degenerative disc and joint diseases, bone spurs, back and joint pain, tendinitis, muscle pain and stiffness, myofascial pain; post surgical complications, such as swelling, inflammation, scarring and stiffness; acute trauma and chronic post-traumatic conditions in the soft tissues and bones, including sprains, strains, wounds, whiplash; repetitive strain injuries such as carpal tunnel syndrome, tennis and golfer's elbow; neurological and neuromuscular conditions; dermatological conditions such as burns, acne, herpes simplex, and ulcers, including infected or non-infected chronic ulcers of different etiology such as venous ulcers, diabetic ulcers, decubitus ulcers, pressure sores, burns and post-traumatic ulcers.

Figure 1:
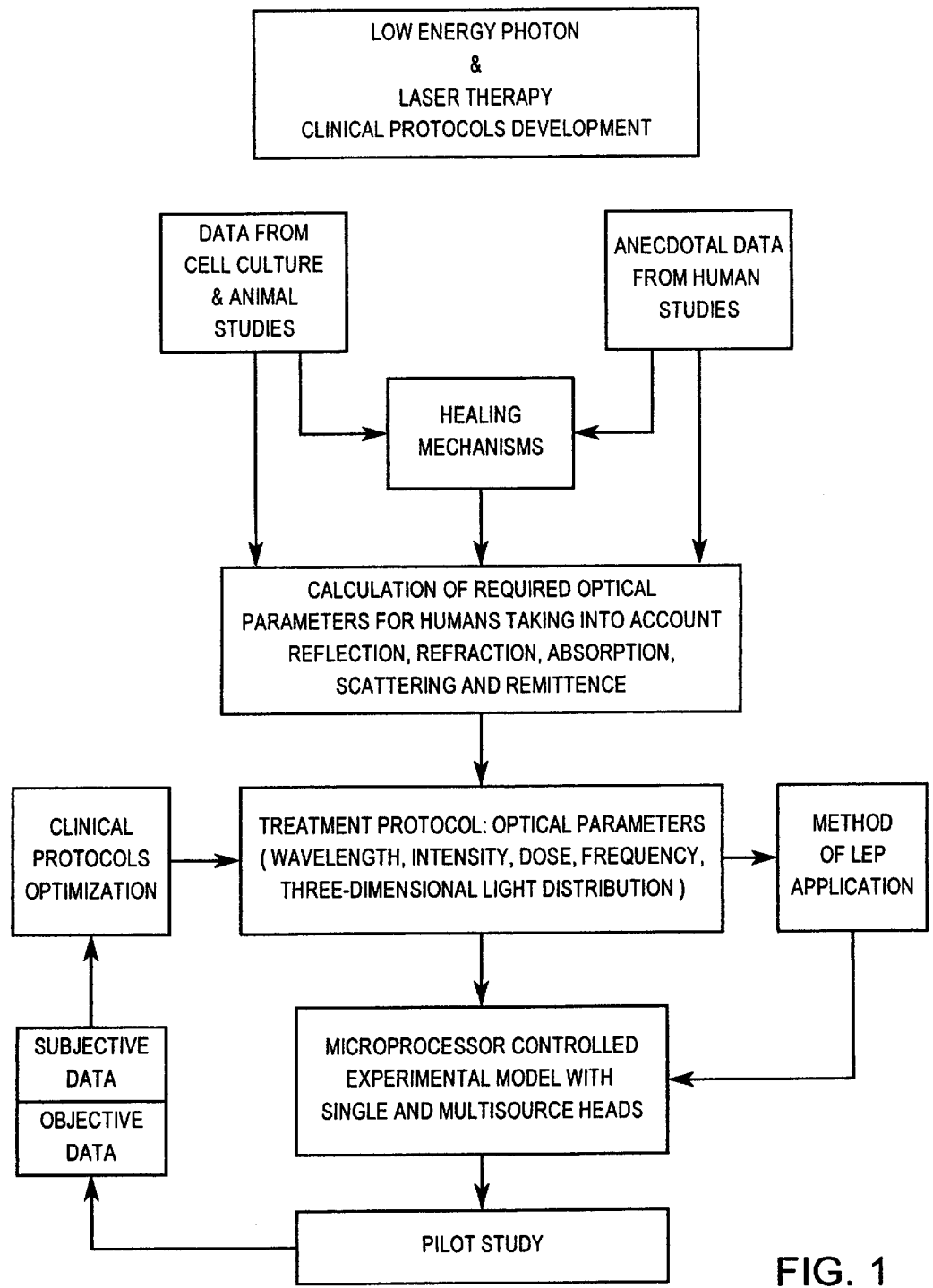
FIG. 1 is a schematic flow chart illustrating the development of LEPT optical parameter protocols.

There are many optical parameters, including the type of the light source, optical power, intensity, dose, frequency and pulse duration, wavelength and bandwidth, beam diameter and divergence, three-dimensional light distribution etc. which may be selected to provide an optimized protocol to treat the disorder. The individual optical parameters may be selected based on the disorder to be treated, as described below. The development of appropriate treatment protocols was carried out as indicated by the flow chart of FIG. 1.

Optical Power

Optical power may be provided in continuous wave mode or pulse mode. In continuous wave mode for a single optical source, optical power P is a total energy of emitted light per second and measured in Watts (W) or Milliwatts (mW). The total power $P_t$ in a cluster probe is $$P_t = n \times P \tag{1}$$

P is the power of a single optical source, and n is the number of optical sources per probe.

The power of a single optical source or cluster probe has to correspond to the type of tissue disorder to be treated. For example, for the treatment of so-called acupuncture points or spinal nerve roots, less power in a single probe is required compared to the treatment of trigger points. The total power in a cluster should be physiologically justified and can vary from application to application. For example, neck and face areas are more sensitive, in general, to LEPT compared to the rest of the body and, therefore, their treatment requires less power in the cluster probe. There is some maximum total power in a cluster probe for every particular wavelength up to which patients can respond to LEPT with comfort. Exceeding certain limits in the total power of a cluster probe could lead to overdose, excessive stress for the patient and sometimes to exacerbation of the patient's condition.

Optical sources in a pulsed mode are described by peak power Pp, average power Pav, pulse frequency F(Hz) and pulse duration τ(s). Average power Pav is less than peak power Pp and can be controlled by changing the frequency in accordance with the following formula $$P_{av} = Pp \times F \times \tau \tag{2}$$

Power by itself is not a decisive factor for LEPT, the power density (intensity $mW/cm^2$) is more important for "photobiomodulation" phenomena. Physiologic tissue response first of all depends on light intensity and dose. Intensity ($mW/cm^2$), and dose ($J/cm^2$) are optical parameters which skin or biotissue can "feel".

Table 1 below shows suitable power ranges for different tissue pathologies.

TABLE 1

| Tissue pathology, area (points) to be treated | | Wavelength range, (nm) | Single optical probe. Range of powers (mW) | Cluster probe. Range of powers (mW) |
|---|---|---|---|---|
| Spinal nerve roots | | 800–1,100 | 1–70 | — |
| Tender trigger points | a) | 630–700 | 5–50 | — |
| | b) | 800–1,000 | 5–150 | |
| Ulcer, wound | a) | 630–700 | 5–30 | 30–150 |
| | b) | 800–1,100 | 10–50 | 30–200 |

TABLE 1-continued

| Tissue pathology, area (points) to be treated | | Wavelength range, (nm) | Single optical probe. Range of powers (mW) | Cluster probe. Range of powers (mW) |
|---|---|---|---|---|
| Acute post-traumatic inflammation in soft tissue (all body, except face) | a) b) | 630–700 800–1,100 | — — | 30–150 50–200 |
| Chronic inflammation (flare-up stage) in soft tissue (all body except face) | | 800–1,100 | — | 20–100 |
| Chronic inflammation (no flare-up) in soft tissue (all body except face) | | 800–1,100 | — | 50–200 |
| All types of inflammation in face soft tissues | a) b) | 630–700 800–960 | — — | 20–50 30–100 |

Intensity (Power Density)

Intensity is the rate of light energy delivery to 1 cm$^2$ of skin or biotissue. Intensity is measured in milliwatts per cm$^2$ (mW/cm$^2$). Real intensity on the skin surface depends on light reflection and scattering from the skin and underlying tissue layers. The light intensity on the skin surface can be calculated with the following formula $$I = (I-R) \times 4 \times P/\pi d^2 \quad (3)$$

where P (or Pav for pulsed mode) is the optical power, d(cm) is the beam diameter and R is the reflection coefficient. Coefficient R can vary from 0.4 up to 0.75 for different wavelengths and depends also on the skin type and condition. For applications using non-contact techniques a portion of the optical power (and dose) equal to R×P is lost because of the reflection. Back scattering has to be taken into account for LEPT dosimetry as well. For contact technique applications, less power is lost due to the repeating light reflection back to the skin surface from optical source parts. Therefore, for the same optical source LEPT dosimetry would be different depending on the type of technique used (contact or noncontact). Particular "photobiomodulation" phenomenon can best be activated within narrow ranges of parameters (e.g. see Tables 2, 5, which appear later in this description). For example, collagen type 1 production is thought to be affected by LEL in an inverse manner to fibroblast proliferation: when cell proliferation is increased, collagen type 1 production is decreased and vice versa (van Breugel and Bar, 1992, Laser Surg. Med. 12:528–537). In cell culture experiments thin cell layers are usually uniformly exposed to light therefore intensity does not change significantly within the sample. For biotissue stimulation, the whole picture is different because light intensity (and dose) decreases with depth z. In the skin and subcutaneous tissue layers light intensity can be approximately described by the following formula (Beer's law):

$$I(z) = I_0(I - R)\exp(-\alpha z) \quad (4)$$

$$I(z) = \frac{(I - R) \times 4 \times P \times \exp(-\alpha z)}{\pi d^2}$$

where I(z)(w/cm$^2$ or mw/cm$^2$)—is the fluence rate (intensity or power density) at the depth z (mm); $I_o$=P/S—incident intensity; P—beam power; S=$\pi d^2$/4 is a beam area for a cylindrical parallel beam of diameter d (cm); and $\alpha$ (mm$^{-1}$) is the attenuation coefficient which depends on light absorption and scattering. This formula may be used to calculate intensity and dose for every particular tissue layer.

Suitable intensities for biostimulation are in the range of from 0.1 to 5,000 mW/cm$^2$. For stimulating healing of chronic ulcers or wounds intensity may preferably be in the range of from 0.2 to 10 mW/cm$^2$, for ulcers or wounds in acute inflammatory stage a preferred range is from 10.0 to 30 mW/cm$^2$ and for infected wounds a preferred range is from 50 to 80 mW/cm$^2$. Table 2 below shows suitable ranges of intensities for different tissue pathologies.

TABLE 2

Ranges of Intensities for Different Tissue Pathologies

| Protocol # | Tissue pathology, area (point) to be treated | Wavelength range, nm | Intensity range mW/cm$^2$ |
|---|---|---|---|
| 1 | 1 Ulcers or wounds, stimulation of repair processes | 2 630–700 | 3 0.2–10 |
| 2 | Ulcers, wounds, acute inflammatory condition | 630–700 | 10–30 |
| 3 | Infected wounds | 630–700 | 50–80 |
| 4 | Area of ulcers or wounds with impaired microcirculation, or to treat such areas and also the area surrounding the ulcer, wound | 800–1,100 | 300–600 |

TABLE 2-continued

Ranges of Intensities for Different Tissue Pathologies

| Protocol # | Tissue pathology, area (point) to be treated | | Wavelength range, nm | Intensity range mW/cm² |
|---|---|---|---|---|
| 5 | Post-surgical scar, acute inflammatory condition | | 630–700 | 10–30 |
| 6 | Post-surgical scar, sub-acute inflammatory condition | | 800–1,100 | 10–40<br>60–100<br>300–600<br>1,000–5,000 |
| 7 | Herpes simplex and acne | | 630–700 | 20–60 |
| 8 | Acute post-traumatic inflammation in soft tissue | a)<br>b) | 630–700<br>800–1,100 | 10–40<br>30–100 |
| 9 | Post-traumatic condition in soft tissue accompanied by hematoma, bruise | | 630–700 | 20–50 |
| 10 | Post-traumatic condition, sub-acute stage | | 800–1,100 a)<br>b)<br>c)<br>d) | 10–40<br>60–100<br>300–600<br>1,000–5,000 |
| 11 | Post-traumatic condition, regeneration of tissue, normalization of function | | 800–1,100 a)<br>b)<br>c) | 60–100<br>300–600<br>1,000–5,000 |
| 12 | Chronic inflammation in soft tissue (flare-up stage), treatment of the affected area | a)<br>b) | 630–700<br>880–1,100 | 1–5<br>1–10 |
| 13 | Chronic inflammation in soft tissue (flare-up stage), treatment at selected points* or areas** on the body | | 630–700<br>800–1,100 | 1–10<br>10–30<br>100–300 |
| 14 | Chronic inflammation in soft tissue (no flare-up) | a)<br>b) | 630–700<br>800–1,100 | 5–30<br>10–40<br>60–100<br>300–600<br>1,000–5,000 |
| 15 | Degenerative joint diseases (arthritis, rheumatoid arthritis, degenerative disk disease, etc.), treatment of the affected area. | | 630–700<br>800–1,100 | 1–10<br>10–30<br>60–100<br>300–600<br>1,000–5,000 |
| 16 | Degenerative joint diseases (arthritis, rheumatoid arthritis, degenerative disk disease, etc.), treatment of selected points* or area(s)** on the body | | 630–700<br>800–1,100 | 1–10<br>100–300 |
| 17 | Muscle spasm relief | a)<br>b) | 630–700<br>800–1,000 | 1–10<br>1–40<br>60–100<br>300–600<br>1,000–10,000 |
| 18 | Localized pain relief | | 800–1,100 | 60–100<br>300–600<br>1,000–10,000 |
| 19 | Tender, trigger point therapy | | 800–1,100 | 300–600<br>1,000–10,000 |
| 20 | So called acupuncture point therapy | a)<br><br><br>b) | 630–700<br><br><br>800–1,100 | 1–10<br>60–100<br>300–600<br>3–15<br>60–100<br>300–600 |
| 21 | Carpal tunnel syndrome | | 800–1,100 | 1–10<br>60–100<br>300–600<br>1,000–10,000 |
| 22 | Neuritis, neuralgia, trigeminal neuralgia | | 800–1,100 | 1–10<br>20–40<br>100–400<br>800–3,000 |
| 23 | Post-traumatic, post-surgical complications, arthritis accompanied by swelling, edema, pain | | 630–700<br>800–1,100 | 10–40<br>300–600<br>1,000–5,000 |

*Selected points on the body may include tender and trigger points, related acupuncture points, spinal nerve roots, points along related nerves' pathways.
**Selected area(s) on the body may include related dermatomes, spine areas, nerves' pathways.

Beam Diameter and Divergence

Beam diameter and divergence are important features of single optical sources. Beam size affects light intensity values on the skin surface and within the tissue in accordance with formulae (3, 4). Beam divergence affects light distribution and dosimetry for different tissue layers. For non-contact techniques light spot size and irradiated area S on the skin surface depend on the distance to the irradiated surface h as follows:

$$S = \frac{\pi}{4} \times (d + 2h \times TAN\alpha)^2 \quad (5)$$

where d is the beam diameter near the probe tip, $2\alpha$ is the diverging angle, $2h \times TAN\ \alpha$ is the additional beam diameter due to beam divergence.

Different optical sources (lasers, laser diodes, light emitting diodes, etc.) have different beam divergences. Lasers usually have small beam divergency, laser diodes and LED's have bigger divergences. For different applications particular beam divergences are more convenient. For example, for the treatment of wounds and ulcers, almost parallel beams are less desirable because of the large areas to be treated, and optical sources with some particular divergence are more convenient.

The beam diameter and divergence should be selected based on the three dimensional size and shape of the tissue area affected. Preferably, the beam diameter and divergence should be selected such that the area receiving LEPT is just slightly larger in size than the area affected. The appropriate radius of the beam may be calculated by the following formula:

$$(R+1)^2/R^2$$

where R (cm) equals the radius of the area affected by the disorder. In the case of lesions, such as ulcers or other open skin wounds, it is particularly important that too large an area not be illuminated as, where the illuminated area is much larger than the lesion, the skin ulcer (wound) healing rate is not optimized. As the ulcer is treated and healed the area requiring treatment and the beam diameter will have to be reduced.

Dose

The dose D is the light energy provided to the unit of surface (1 cm$^2$) during a single irradiation and measured in J/cm$^2$ or mJ/cm$^2$. The light dose received by the skin surface is $$D = I \times t \quad (6)$$

where I is the intensity on the skin surface, and t is the exposure time(s). The dose received by subcutaneous tissue layer at the depth z for a parallel beam can be calculated by the following formula:

$$D = I(z) \times t \quad (7)$$

where I(z) is given by formula (4).

As mentioned above, the dose alone does not ensure particular photoeffect or healing phenomenon. Only proper selection of the whole set of optical parameters including dose will provide the desirable therapeutic effect. The selection of optical parameters depends on the medical condition, location of the affected areas, person's age, etc. Particular examples will be provided below.

Figure 2:
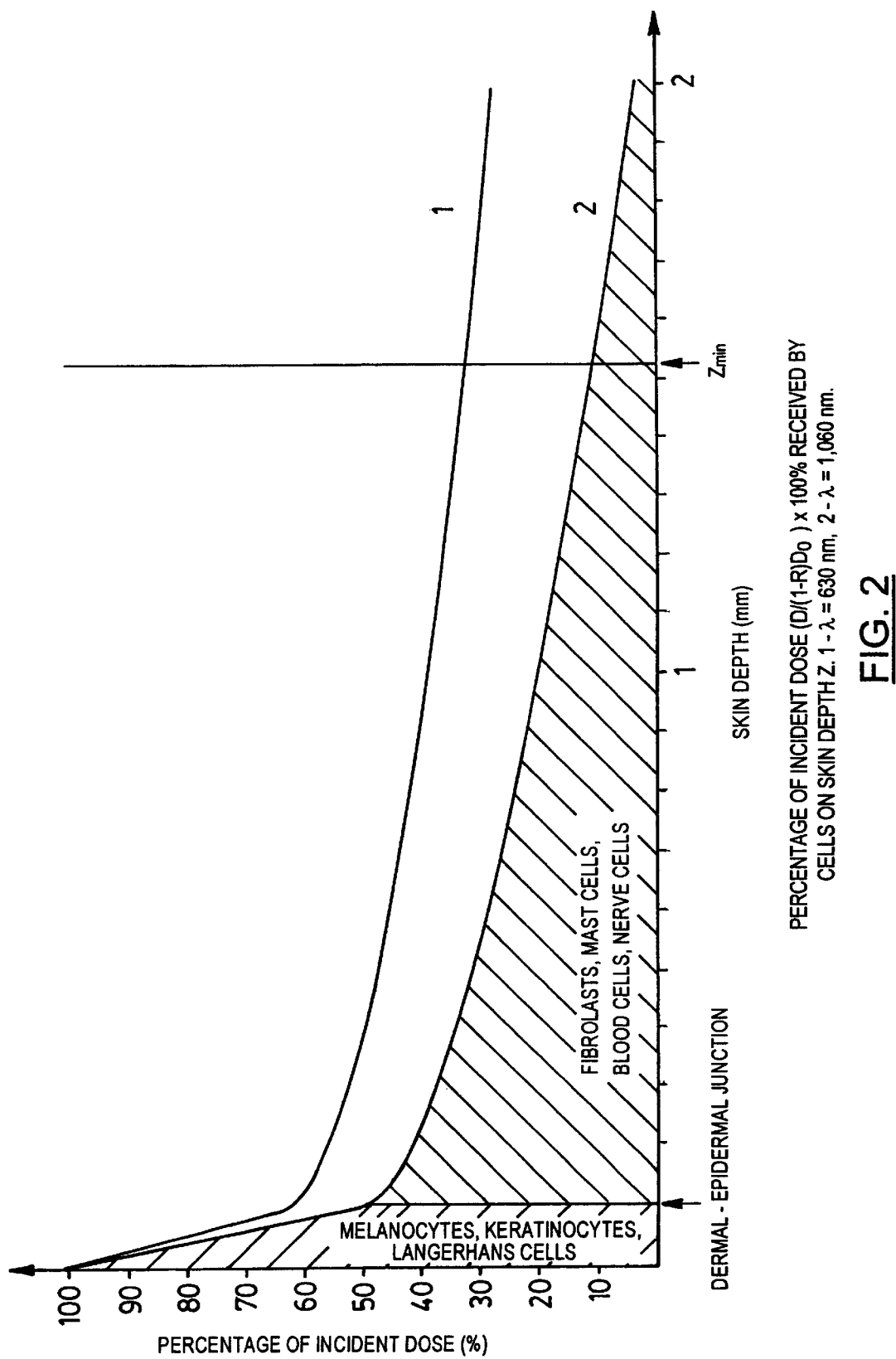
FIG. 2 is a graph showing the percentage of the dose on the skin surface $(D-(z-)/(1-R)D_o)\times 100\%$ received by cells at skin depth $\overline{Z}$ and at wavelengths $\lambda$=630 nm (wavelength 1) and $\lambda$=1,060 nm (wavelength 2), (for explanation of parameters $D_o$, D and R see the following detailed description)

The percentage of dose $(D(z)/(1-R)D_o) \times 100\%$ on the skin surface received by cells at a skin depth $\overline{Z}$ at wavelengths of 630 nm and 1,060 nm is shown in Table 3 and is illustrated in FIG. 2. All curves D(z) for different wavelengths in the interval (630–1,060) nm depend on corresponding reflectance $R_\lambda$ and attenuation $\alpha_\lambda$ coefficients (see Table 4) and are located between curves 1 and 2 on FIG. 2.

1. D(J/cm$^2$) is the actual dose (fluence) received by cells at depth $\overline{z}$.

2. $R = R_s + R_T$—diffuse reflectance $R_s$—regular reflectance from the skin surface $R_T$—is the remittance from within the tissue 3. $D_o = I_o \times t$—conventionally calculated dose t=exposure time 4. $I_o = P/S$—incident intensity (P—beam power; S—beam area)

The actual doses received by different cell types in the skin exposed to LEPT are illustrated in Table 3. The maximum dose $(D \sim (0.5-1.3)\ D_o$ is received by keratinocytes and Langerhans cells from the epidermis. Cells from dermis (fibroblasts, mast cells, blood and nerve cells are exposed to significantly less dose than the incident one $D \sim (0.5-0.3)\ D_o$. The least dose $D \sim 0.3 D_o/t$ is received by blood cells moving through capillaries (velocity~1 mm/sec).

TABLE 3

Actual dose received by different cells in the skin exposed to LEP radiation

| Cell type | Formulae for actual dose calculation | Typical range of doses |
|---|---|---|
| Keratinocytes Langerhans cells | (0.5–1.8) D$_0$ (1-R) | (0.5–1.3) D$_0$ |
| Fibroblasts mast cells nerve cells not moving blood cells | (0.05–0.5) D$_0$ (1-R) | (0.05–0.3) D$_0$ |
| moving blood cells | (0.05–0.5) D$_0$ (1-R) × (2/t) | 0.3 D$_0$/t | where D$_0$ (1/cm$^2$) is a conventionally calculated dose

TABLE 4

Diffuse reflectance R$_\lambda$, attenuation coefficients $\alpha_\lambda$ and penetration depths d$_\lambda$ for some wavelengths

| $\lambda$ (nm) | R$_\lambda$ | I-R$_\lambda$ | $\alpha_\lambda$ (mm$^{-1}$) | d$_\lambda$ (mm) |
|---|---|---|---|---|
| 630 | 0.6 | 0.4 | 1.6 | 0.6 |
| 820 | 0.5 | 0.5 | 1.0 | 1 |
| 900 | 0.45 | 0.55 | 0.8 | 1.25 |
| 1,060 | 0.5 | 0.5 | 0.6 | 1.7 | d(mm) - penetration depth
$\alpha_\lambda d_\lambda = I$
$I(d) = 0.37 I_o$

Suitable doses for photobiomodulation are in the range of from 0.1 to 20 J/cm$^2$, preferably from 0.2 to 5 J/cm$^2$. For stimulating healing of chronic ulcers or wounds doses may preferably be in the range of from 0.05 to 0.2 J/cm$^2$, for ulcers or wounds in acute inflammatory stage a preferred range is from 2 to 5 J/cm$^2$ and for infected wounds a preferred range is from 3.0 to 7.0 J/cm$^2$. See Table 5 below for ranges and doses (in Joules/cm$^2$) for different tissue pathologies.

TABLE 5

Ranges of doses for different tissue pathologies

| Protocol # | Tissue pathology, area (point) to be treated | Wavelength range, nm | Dose range, J/cm$^2$ |
|---|---|---|---|
| 1 | 2 | 3 | |
| 1 | Chronic ulcers or wounds, stimulation of healing | 630–700 | 0.05–0.2 |
| 2 | Ulcers, wounds, acute inflammatory condition | 630–700 | 2–5 |
| 3 | Infected wounds | 630–700 | 3–9 |
| 4 | Area of ulcers or wounds with impaired microcirculation, or to treat such area and also the area surrounding the ulcer, wound | 800–1,100 | 0.1–9 |
| 5 | Post-surgical scar, acute inflammatory condition | 630–700 | 2–5 |
| 6 | Post-surgical scar, sub-acute inflammatory condition | 800–1,100 | 3–7 4–25 |
| 7 | Herpes simplex and acne | 630–700 | 4–9 |
| 8 | Acute post-traumatic inflammation in soft tissue | a) 630–700 b) 800–1,100 | 3–9 3–10 |
| 9 | Post-traumatic condition in soft tissue accompanied by hematoma, bruise | 630–700 | 5–14 |
| 10 | Post-traumatic condition, subacute stage | 800–1,100 | 3–7 4–25 |
| 11 | Post-traumatic condition, regeneration of tissue, normalization of function | 800–1,100 | 3–5 4–25 |
| 12 | Chronic inflammation in soft tissue (flare-up stage), Treatment of the affected area NS NF 12.18.96 | a) 630–700 b) 880–1,100 | 0.1–0.5 0.1–0.5 |
| 13 | Chronic inflammation in soft tissue (flare-up stage), treatment of selected points* or area(s)** on the body | 630–700 800–1,100 | 0.1–0.6 1–5 |
| 14 | Chronic inflammation in soft tissue (no flare-up) | a) 630–700 b) 800–1,100 | 2–7 2–9 3–25 25–100 |
| 15 | Degenerative joint diseases (arthritis, rheumatoid arthritis, degenerative disk disease, etc.), treatment of the affected area. NS NF 12.18.96 NF NS 12.18.96 | 630–700 800–1,100 | 0.1–0.5 2–9 3–25 25–100 |
| 16 | Degenerative joint diseases (arthritis, rheumatoid arthritis, degenerative disk disease, etc.), treatment of selected points* or area(s)** on the body | 630–700 800–1,100 | 0.1–0.5 1–5 |
| 17 | Muscle spasm relief | a) 630–700 b) 800–1,100 | 0.1–0.3 0.1–0.5 3–5 4–25 25–100 |
| 18 | Localized pain relief | 800–1,100 | 8–150 |
| 19 | Tender, trigger point therapy | 800–1,100 | 4–150 |
| 20 | So-called acupuncture point therapy | a) 630–700 b) 800–1,100 | 0.02–0.2 0.1–1.0 2–4 0.06–0.4 0.1–2.0 2–4 |
| 21 | Carpal tunnel syndrome | 800–1,100 | 0.05–0.3 0.2–4.0 5–10 25–150 |
| 22 | Neuritis, neuralgia, trigeminal neuralgia | 800–1,100 | 0.1–0.3 1–3 5–25 25–80 |
| 23 | Post-traumatic, post-surgical complications, arthritis, accompanied by swelling, edema, pain | 630–700 800–1,100 | 5–14 25–100 |

*Selected points on the body may include tender and trigger points, related acupuncture points, spinal nerve roots, points along related nerves' pathways.
**Selected area(s) on the body may include related dermatomes, spine areas, nerves' pathways.

Frequency and Pulse Duration

Low range frequencies of 0–200 Hz may sensitize release of key neurotransmitters and/or neurohormones (e.g. endorphins, cortisol, serotonin). These frequencies correspond to some basic electromagnetic oscillation frequencies in the peripheral and central nervous system (brain). Once released these neurotransmitters and/or neurohormones can modulate inflammation, pain or other body responses. Analogous phenomena can be expected with "photobiomodulation" within the same range of low frequencies. Certainly, the interaction between living cell and pulsed electromagnetic wave depends on wavelength as well as pulse duration. Pulse repetition rates within the range 1,000–10,000 Hz with different pulse durations (milli-, micro- or nanoseconds) can be used to change average power. Specific pulse repetition rates to induce particular healing mechanism are reflected in Table 6 below.

TABLE 6

Ranges of frequencies for stimulation of particular healing mechanisms

| Healing mechanisms stimulated | Basic frequency (Hz) or continuous wave mode | Endogenous modulation frequency (Hz) |
|---|---|---|
| Endorphin release | 1–5 | — |
| Capillar microcirulation improvement | 9–11 | 1–1.2 (average frequency of heart beating) |
| | 50–200 | 0.2–0.3 (average frequency of breathing cycle) |
| Localized muscle spasm and pain relief | 50–120 or Continuous wave mode | 1–5 0.2–0.3 |
| Lymph flow enhancement | continuous wave mode | 1–1.2 0.2–0.3 |
| Stimulation of tissue repair | continuous wave mode or 100 Hz | 1.2 0.2–0.3 |

Three Dimensional Light Distribution

Depending on the target tissue for LEPT (e.g. skin, muscle, ligament) a proper three-dimensional light distribution should be provided to get the desirable physiologic and therapeutic response. For single optical sources important parameters affecting light distribution are beam size, divergence, light wavelength as well as biotissue optical properties (reflection, absorption, scattering, refraction). Total reflectance is equal to the sum of the regular reflectance from the skin surface and the remittance from within the tissue (see FIG. 4).

For cluster probes, additional contributive parameters are the distance between diodes and the cluster probe's three-dimensional shape. All these parameters should be physiologically justified to provide optimal biotissue response and requirable three-dimensional light distribution. For example, the distance between diodes can affect vasoactive blood vessel response and average energy density delivered to the treated area. For proper vasoactive response a definite distance between diodes has to be provided depending on particular parameters of a singular diode (power, beam, diameter, divergence).

Figure 3:
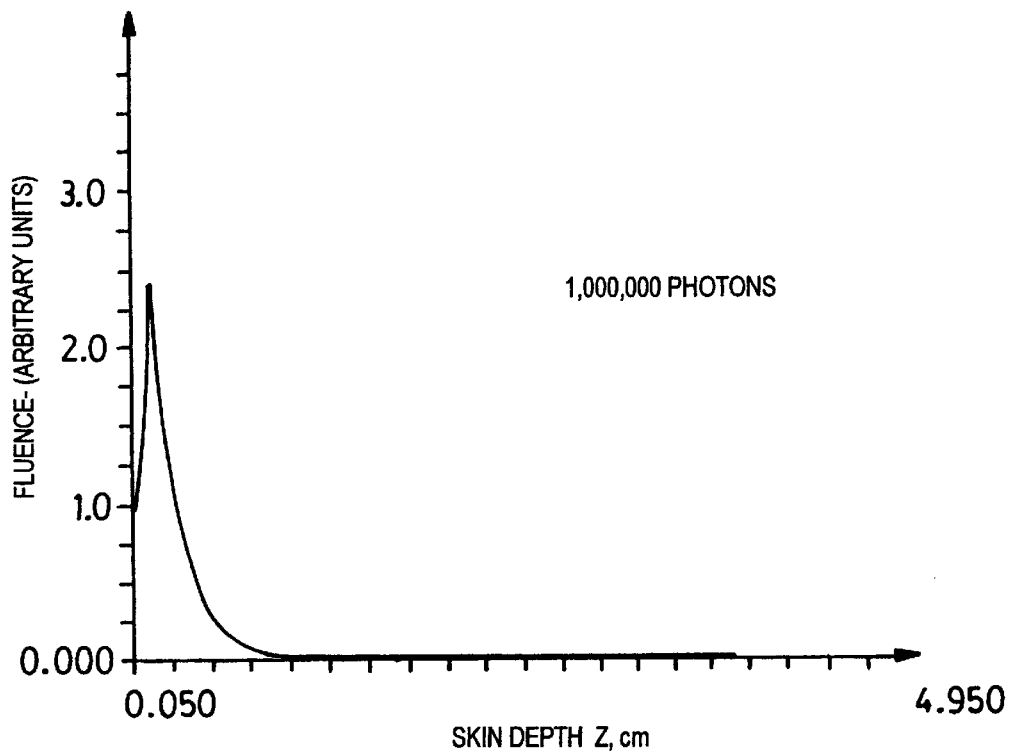
FIG. 3 is a graph showing the results of Monte-Carlo simulation of photon propagation in the skin.
Figure 4:
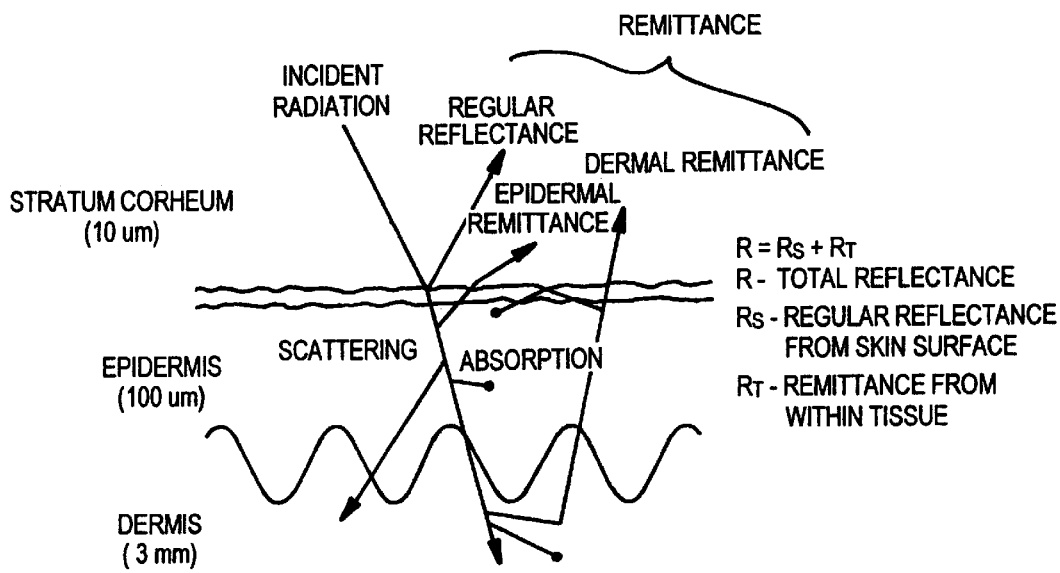
FIG. 4 is a schematic view showing major optical pathways in human skin.

The three-dimensional light distribution in tissues such as the skin and underlying tissue layers may be calculated based on diffusion approximation and/or the Monte Carlo approach (L. Wang and S. Jacques, Hybrid model of Monte Carlo Simulation and diffusion theory for light reflectance by turbid media, J. Opt. Soc. Am. A/Vol. 10, No. 8, 1993, pp 1746–1752; A. Welch et al., Practical Models for Light Distribution in Laser-Irradiated Tissue, Lasers in Surg. Med. 6: 488–493, 1987). Results of Monte-Carlo stimulation of photon propagation in the skin with a flat beam, R=1 cm are shown in FIG. 3. Examples of diffuse reflectance R$\lambda$, attenuation coefficients $\alpha\lambda$ and penetration depths d$\lambda$ for some wavelengths are shown in Table 4. A schematic representation of the major optical pathways in human skin is shown in FIG. 4.

Wavelength

Wavelength $\lambda$ (nm) is the basic electromagnetic wave feature which is directly linked to the energy of an individual light quantum (photon). The more wavelength the less photon energy. Wavelength is also linked to the monochromatic light color. Visible monochromatic light changes its color with wavelength, increasing from violet and blue (shorter wavelengths) to orange and red (longer wavelengths). Cell culture experiments have indicated that there is a selectivity in photoinduced phenomena related to wavelengths. Experiments on different cell cultures (microbe and mammalian) have revealed the ranges of wavelengths (360–440 nm, 630–680 nm. 740–760 nm) where photoinduced phenomena are observed (Karu, Health Physics, 56:691–704, 1989; Karu, *IEEE J. of Quantum Electronics*, QE23:1703–1717, 1987). Photoeffect can be induced by monochromatic light, only in cases, where a cell contains photoacceptors, substances which are able to absorb monochromatic light of this particular wavelength. No photoinduced cell phenomena can be observed if there are no wavelength specific photoacceptors in a cell.

The following factors have to be taken into account when considering LEPT dosimetry for monochromatic light of a particular wavelength $\lambda$. The dose required for "photobiomodulation" strongly depends on the wavelength. In general, the longer the wavelength the more dose is required to induce photoeffect. For example, in experiments on cell cultures, doses required for DNA synthesis stimulation are 10–100 times less with blue light ($\lambda$=404 nm) than with red ($\lambda$=680 nm) or near infrared ($\lambda$=760 nm) light.

Wavelengths in the range of from 400 to 10,000 nm may be used for LEPT, preferably from 500 to 2,000, more preferably from 600 to 1,100, most preferably from 600 to 700 nm and 800–1,100. There appears to be some optimal wavelength range to induce every particular photoeffect or p healing phenomenon. For example, light having a wavelength of from 600 to 700, preferably from 630–680 nm, may be used for wound and ulcer healing. For chronic soft tissue pathology monochromatic light in near infrared wavelength range (800–1,100) is more suitable.

Biotissue optical parameters (reflection, scattering, refraction, absorption and depth penetration) depend on wavelength. Therefore, light wavelength affects three-dimensional light distribution in biotissue. For example in a specific wavelength range, the longer wavelength the more light penetration depth. The darker skin the more light absorption, therefore the dose for a black skin has to be less then for a white skin.

Monochromaticity (Bandwidth)

Light source is described by its spectrum, which shows the range of wavelengths of the emitted light. Strictly monochromatic light source is a source of radiation with exactly the same wavelengths. This is never achieved in practice even with a laser. Every light source can be described by its spectrum bandwidth $\Delta\lambda$(nm). The smaller the bandwidth the more monochromaticity of the light source. The following considerations are important in regards to light source monochromaticity.

Biological objects became adapted to wide-band solar radiation through evolution. Therefore, pronounced photoinduced phenomena in living cells can be observed only under irradiation by a light source with narrow enough bandwidth. The exact restrictions on light bandwidth may differ for various biological objects.

Simultaneous irradiation by wide bandwidth and monochromatic light can lead to decrease or even disappearance of "photobiomodulation" effect. Therefore, it is recommended to provide some LEPT treatments in a darkened room.

Difference in wavelengths emitted by optical source is leading to dispersion in light reflection, scattering, refraction and absorption which can affect three-dimensional light distribution and LEPT dosimetry.

Bandwidth of the optical source can affect optimal intensity and dose values required to induce a particular healing phenomenon. The full bandwidth of monochromatic light to activate healing phenomena should not exceed 30–40 nm.

Selection of Optical Parameter Protocols for LEPT

Optical parameter protocols, may be established by combining the above-noted parameters. Once established the protocols may be entered and stored in the central microprocessor. A user of the apparatus can then select the appropriate protocol for the disorder to be treated. The clinical practitioner must examine the patient, establish diagnosis and the following particulars of tissue pathology:

(a) for musculoskeletal conditions:
  (i) the stage of inflammatory process (acute, subacute inflammation, chronic inflammation with or without flare-up of preexisting pathological condition)
  (ii) localization of soft tissue affected areas, muscle spasm, tender and trigger points
(b) for skin conditions:
  the stage of inflammatory process (acute or chronic inflammation, presence or absence of bacteria contamination)

LEPT optical parameters are chosen from Tables 1–3, 5–7, based on diagnosis and soft tissue condition.

Some suitable protocol ranges are shown in Table 7 below.

TABLE 7

| Wave-length | Power | Beam Diameter or Covered Area Size | Intensity | Dose |
|---|---|---|---|---|
| Red | (1–40) mW | (0.1–15) cm | (1–220) mW/cm$^2$ | (0.05–20) J/cm$^2$ |
| Infrared | (10–200) mW | (0.1–15) cm | (1–1220) mW/cm$^2$ | (0.5–150) J/cm$^2$ |

Intensity and dose are important parameters in providing the proper optical parameter protocols to induce photobiomodulation phenomena. The total volume and amount of cells exposed to LEPT depends on the light incident intensity and beam size.

Powers of optical sources used for LEPT differ by one order of magnitude and the rest of the parameters (treated area size, intensity and dose) differ by more than two orders of magnitude from each other. There are other optical parameters which can affect "photobiomodulation" phenomena. To be in a position to repeat particular in vitro or in vivo studies an investigator has carefully to reproduce the same experimental conditions. Failure to control properly all significant optical parameters may lead to nonreproducibility of results both in experiments and clinical trials.

Optical parameter protocols for various disorders were determined by the present inventors and examples of protocols are provided below (see Tables 8, 9 and 10). In Table 8, in the column entitled "Probe", R means red and IR means infrared, and the number refers to the number of optical sources used. Thus, for example, R-7 refers to a probe having 7 light emitting or superluminous diodes, each red. IR-LD means infrared laser or laser diode. Also in Table 8, the "frequency" refers to the light source being continuously on ("CW"—continuous wave mode) or pulsed, in which case the number given is the pulse repetition rate per second.

In Table 9, the "Protocol #" refers to the protocol number in Table 8. When the treatment consists of more than one protocol, they are administered sequentially, in the order shown, one immediately after the other.

TABLE 8

Examples of LEPT protocols for some musculoskeletal and dermatological conditions

| Protocol # | Pathological condition | Probe | Wavelength (nm) | Frequency (Hz) | Single diode power (mW) | Exposure time (sec.) | Note |
|---|---|---|---|---|---|---|---|
| 1 | Chronic ulcers or wounds, stimulation of tissue repair | R-7 R-14 R-16 R-22 | 630–670 | CW or 100 | 4–6 or 2–3 | 130–180 or 130–200 | Hold the probe at the distance 7 cm directly over the ulcer surface |
| 2 | Chronic ulcers or wounds, acute inflammatory condition, infected | R-7 R-14 R-16 R-22 | 630–670 | CW or 100 | 4–6 | 130–200 | Hold the probe in near contact to the ulcer surface |
| 3 | Chronic ulcers, improvement of microcirculation | IR-7 IR-14 IR-16 IR-22 | 800–1,100 | 10 or CW | 6–12 | 20–40 | Contact application on the skin surrounding the ulcer |
| 4 | Acute post-traumatic inflammation in soft tissue | R-7 R-14 R-16 R-22 | 630–700 | CW or 100 | 4–6 | 180–400 | Contact application over the affected area |
| 5 | Acute post-traumatic inflammation in soft tissue | IR-7 IR-14 IR-16 IR-22 | 800–1,100 | CW or 100 | 10–15 | 40–150 | Contact application over the affected area |
| 6 | Whiplash | R-7 R-14 R-16 R-22 | 630–700 | CW or 100, 1.2 | 4–6 | 400–500 | Moving the probe over spine area (C$_2$–T$_4$) at the distance 7 cm with the frequency 5 movements per minute |
| 7 | Whiplash | IR-7 IR-14 IR-16 IR-22 | 800–1,100 | CW or 100, 1.2 | 10–15 | 400–500 | Moving the probe over spine area (C$_2$–T$_4$) at the distance 1 cm with the frequency 5 movements per minute |
| 8 | Chronic inflammation in soft tissue (flare-up stage), arthritis, degenerative disc disease, chronic tendinitis, etc. | R-7 R-14 R-16 R-22 | 630–700 | CW or 100, 1.2 | 4–6 | 120–300 | Hold the probe at the distance 7 cm over the affected area |
| 9 | Chronic inflammation in soft tissue (flare-up stage), arthritis, degenerative disc disease, chronic tendinitis, etc. | IR-7 IR-14 IR-16 IR-22 | 800–1,100 | CW or 100, 1.2 | 10–15 | 150–300 | Hold the probe at the distance 1 cm over the affected area |

TABLE 8-continued

Examples of LEPT protocols for some musculoskeletal and dermatological conditions

| Protocol # | Pathological condition | Probe | Wavelength (nm) | Frequency (Hz) | Single diode power (mW) | Exposure time (sec.) | Note |
|---|---|---|---|---|---|---|---|
| 10 | Chronic inflammation in soft tissue (no flare-up), arthritis, epicondylitis, chronic tendinitis, etc. | IR-7 IR-14 IR-16 IR-22 | 800–1,100 | CW or 100, 1.2 | 4 or 8 or 12 | 300–400 or 200–250 or 90–120 | Hold the probe at the distance 0.2–0.3 cm over the affected area |
| 11 | Chronic inflammation in soft tissue (no flare-up), arthritis, epicondylitis, chronic tendinitis, etc. | IR-7 IR-14 IR-16 IR-22 | 800–1,100 | 100, 1.2 | 10–15 | 20–70 | Contact, over the affected area |
| 12 | Chronic inflammation in soft tissue (no flare-up), arthritis, epicondylitis, chronic tendinitis, etc. | IR-LD | 800–1,100 | CW | 50–200 | 3–30 | Contact, selected points in the affected area |
| 13 | Muscle spasm relief | R-7 R-14 R-16 R-22 | 630–700 | CW or 10 or 100, 1.2 | 4–6 | 120–300 | Hold the probe at the distance 1 cm over the affected area |
| 14 | Muscle spasm relief | IR-7 IR-14 IR-16 IR-22 | 800–1,100 | CW or 10 or 100, 1.2 | 10–15 | 120–300 | Hold the probe at the distance 1 cm over the affected area |
| 15 | Muscle spasm relief | IR-7 IR-14 IR-16 IR-22 | 800–1,100 | 100, 1.2 | 10–15 | 20–50 | Contact, over the affected area |
| 16 | Muscle spasm relief | IR-LD | 800–1,100 | CW | 50–200 | 3–20 | Contact, selected points in the affected area |
| 17 | Carpal tunnel syndrome | IR-7 IR-14 IR-16 IR-22 | 800–1,100 | CW or 100, 1.2 | 10–15 | 120–300 | Hold the probe at the distance 1 cm over the median nerve compression area |
| 18 | Carpal tunnel syndrome | IR-7 IR-14 IR-16 IR-22 | 800–1,100 | CW or 100, 1.2 | 10–15 | 30–120 | Hold the probe at the distance 0.2–0.3 cm over the median nerve compression area |
| 19 | Carpal tunnel syndrome | IR-7 IR-14 IR-16 IR-22 | 800–1,100 | 4 or 100, 1.2 | 10–15 | 20–60 | Contact, over the palm and the median nerve compression area |
| 20 | Carpal tunnel syndrome | IR-1 | 800–1,100 | CW or 100, 1.2 | 12–15 | 25–300 | Contact, selected points in the arm, forearm, hand and points over the median nerve compression area |
| 21 | Carpal tunnel syndrome | IR-LD | 800–1,100 | CW | 50–200 | 5–60 | Contact, selected points in the arm, forearm, hand and points over the median nerve compression area |
| 22 | Neuritis, neuralgia, trigeminal neuralgia | IR-7 IR-14 IR-16 IR-22 | 800–1,100 | CW or 100, 1.2 | 10–15 | 20–100 | Hold the probe at the distance 1 cm over the affected area |
| 23 | Neuritis, neuralgia, trigeminal neuralgia, etc. | IR-7 IR-14 IR-16 | 800–1,100 | 100, 1.2 | 10–15 | 20–40 | Contact, over the affected area |
| 24 | Neuritis, neuralgia, trigeminal neuralgia, etc. | IR-1 | 800–1,100 | CW or 100, 1.2 | 10–15 | 25–160 | Contact, selected points in the affected area |
| 25 | Neuritis, neuralgia, trigeminal neuralgia, etc. | IR-LD | 800–1,100 | CW | 30–150 | 5–40 | Contact, selected points in the affected area |

TABLE 9

Examples of daily treatment schedule:

| Day | 1 | 2 | 3 | 4 | 5 | 6* | 7 | 8 | 9 | 10 |
|---|---|---|---|---|---|---|---|---|---|---|
| 1. Chronic ulcers or wounds, acute inflammatory condition, infected* | | | | | | | | | | |
| Protocol # | 2 + 1 | 2 + 1 | 2 + 1 | 2 + 1 | 2 + 1 | 1 + 3 | 1 + 3 | 1 + 3 | 1 + 3 | 1 + 3 |
| 2. Acute post-traumatic inflammation in soft tissue | | | | | | | | | | |
| Protocol # | 4 | 4 | 4 | 4 | 5 | 5 | 5 | 5 | 5 | 5 |
| 3. Whiplash | | | | | | | | | | |
| Protocol # | 6 + 7 | 6 + 7 | 6 + 7 | 6 + 7 | 6 + 7 | 6 + 7 | 6 + 7 | 6 + 7 | 6 + 7 | 6 + 7 |
| 4. Chronic inflammation in soft tissue (flare-up stage) | | | | | | | | | | |
| Protocol # | 8 or 9 | 8 or 9 | 8 or 9 | 8 or 9 | 8 or 9 | 8 or 9 | 8 or 9 | 8 or 9 | 8 or 9 | 8 or 9 |
| 5. Chronic inflammation in soft tissue (no flare-up) | | | | | | | | | | |
| Protocol # | 10 | 10 | 11 | 11 | 11 + 12 | 11 + 12 | 11 + 12 | 11 + 12 | 11 + 12 | 11 + 12 |
| 6. Muscle spasm relief | | | | | | | | | | |
| Protocol # | 10 or14 | 10 or14 | 11 or15 | 11 or15 | 11 + 12 | 11 + 12 | 11 + 12 | 11 + 12 | 11 + 12 | 11 + 12 |
| 7. Carpal tunnel syndrome | | | | | | | | | | |
| Protocol # | 17 + 20 | 17 + 20 | 18 + 20 | 18 + 20 | 19 + 20 | 19 + 20 | 19 + 21 | 19 + 21 | 19 + 21 | 19 + 21 |
| 8. Neuritis, neuralgia, trigeminal neuralgia | | | | | | | | | | |
| Protocol # | 22 + 24 | 22 + 24 | 22 + 24 | 23 + 24 | 23 + 24 | 23 + 25 | 23 + 25 | 23 + 25 | 23 + 25 | 23 + 25 |

*Administration of protocol #2 is discontinued after resolution of acute inflammation and infection.
R-7, 14, 16, 22 - represent multiple light sources with $\lambda$ = 630–700 nm,
The light sources spacial distribution are shown on FIG. ID., 13
IR-1 represents single monochromatic light source with $\lambda$ = 800–1,100 nm
IR-7, 12, 14, 16, 22 - represent multiple light sources with $\lambda$ = 800–1,100 nm
The light sources spacial distribution are shown on FIG. ID., 13. (CW - continuous wave, 4, 10, 100 Hz are wave frequencies and 1.2 Hz is the modulation frequency for the above CW or other frequencies)
IR-LD represents laser or laser diode with $\lambda$ = 800–1,100 nm

TABLE 10

| | Axon | | | | | DNA & RNA | | | | Membrane thickness |
|---|---|---|---|---|---|---|---|---|---|---|
| Biological structure size (cm) | 0.1 | 0.01 | 0.003 | 0.001 | $3*10^{-4}$ | $10^{-4}$ | $*10^{-5}$ | $10^{-5}$ | $3*10^{-6}$ | $10^{-6}$ |
| Pulse duration (sec) | 10 | 0.1 | 0.01 | 0.001 | $10^{-4}$ | $10^{-5}$ | $10^{-6}$ | $10^{-7}$ | $10^{-8}$ | $10^{-9}$ |

Central Microprocessor

The selected optical parameter protocols may be stored in a central microprocessor, which may be powered by any standard electrical power source.

FIG. 5 shows an illustrative relationship between dosage and intensity in three cases. Reference numeral 1 refers to the relationship between intensity and dosage which may be required for ulcer, wound healing, or smooth scar formation. Block 2 shows the required relationship for ulcer, wound healing in acute and sub acute conditions. Block 3 shows a different relationship which may be required for infected wound healing. Block 4 shows the relationship between intensity and dosage provided by a typical laser, which as will be seen may completely miss the areas needed.

Base Unit and Probe

The selected optical parameter protocols may be stored in a central microprocessor of a base unit, which may be powered by any standard electrical power supply. The base unit may include a keypad for the user input interface and a display for the user output interface. The system contains a microprocessor and 8 kilobytes of non-volatile memory which will normally hold all the optical parameter protocols needed.

Figures 1, 6:
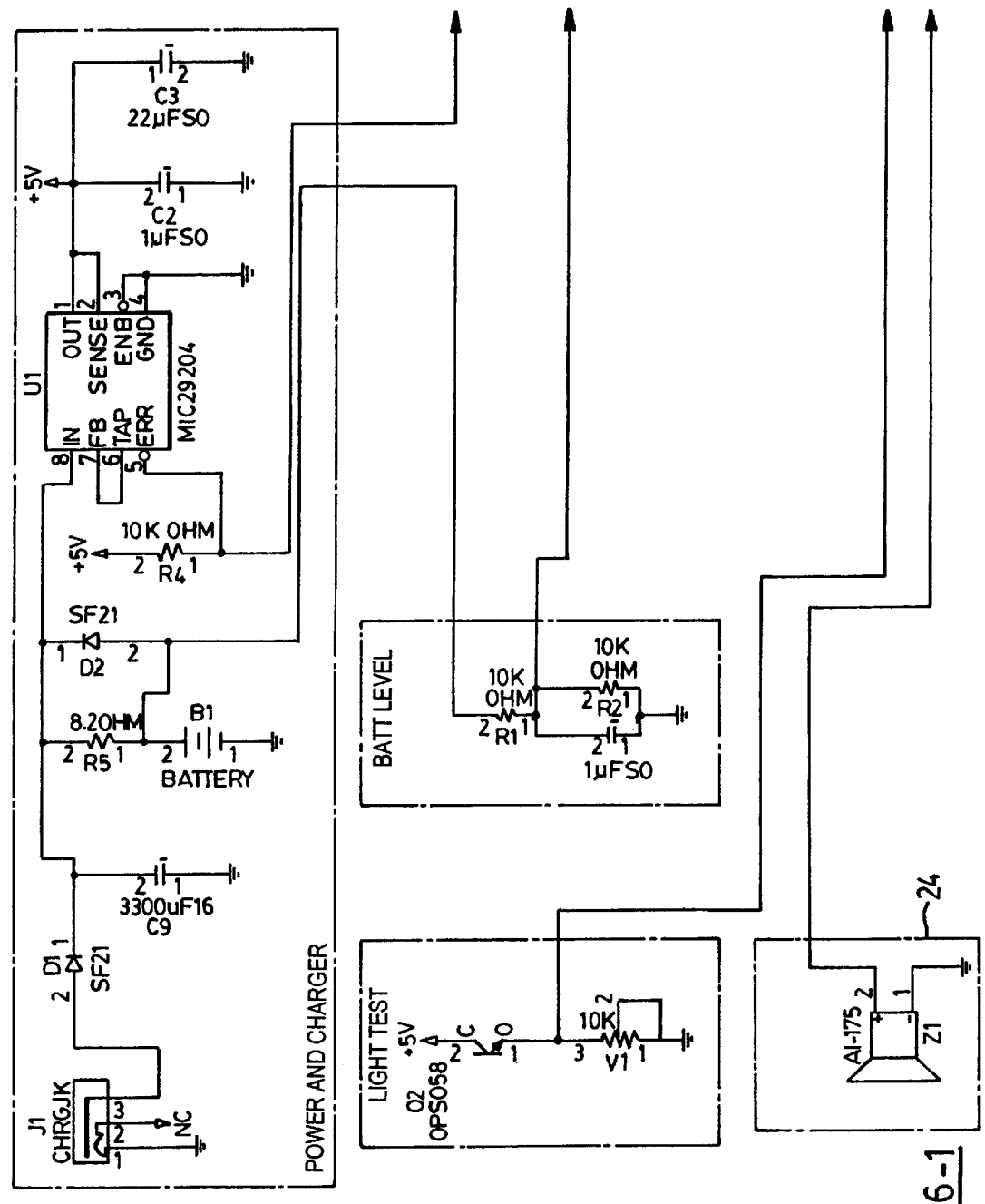
FIG. 6 is a circuit diagram of a base unit according to the invention.
Figures 2, 6:
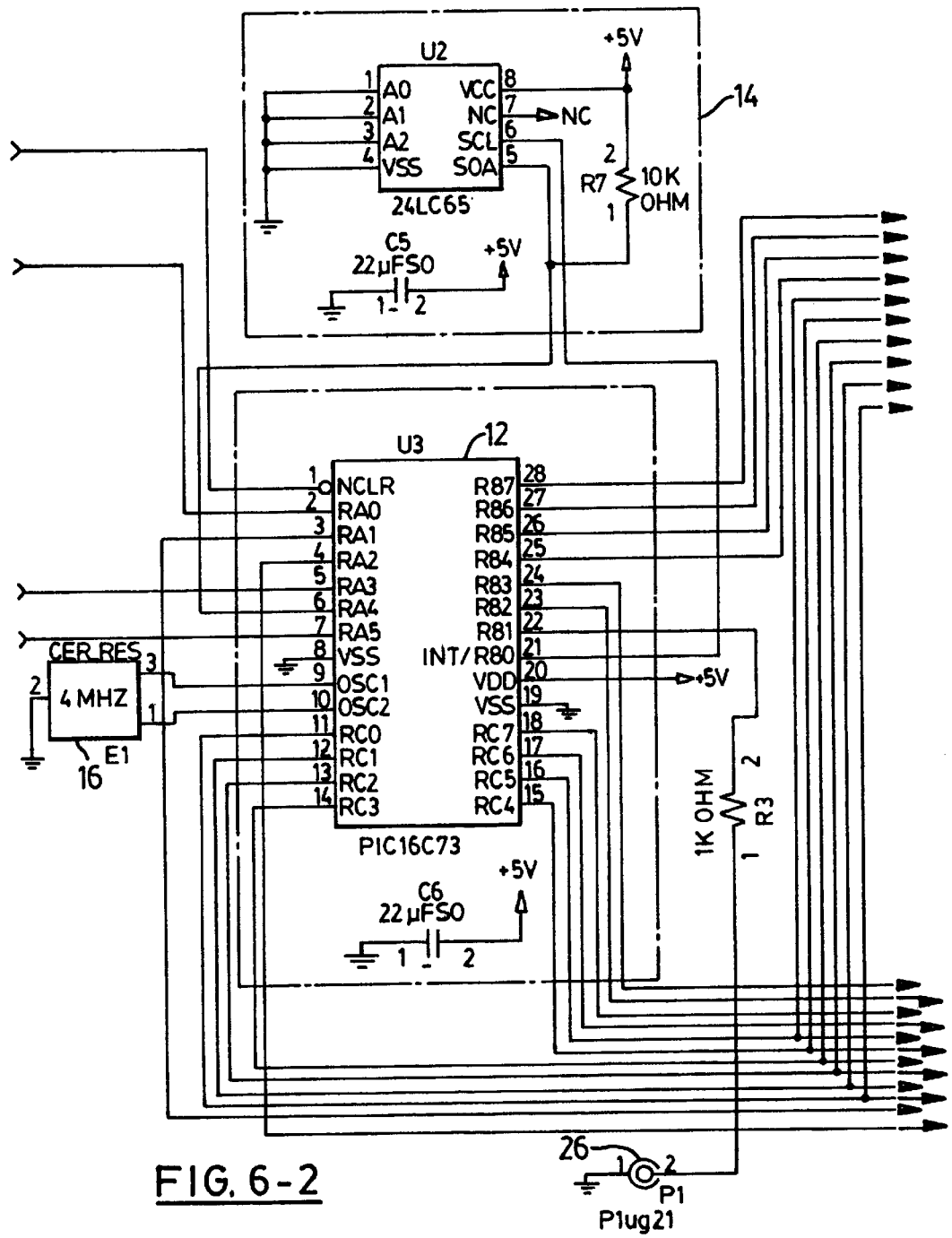
Figures 3, 6:
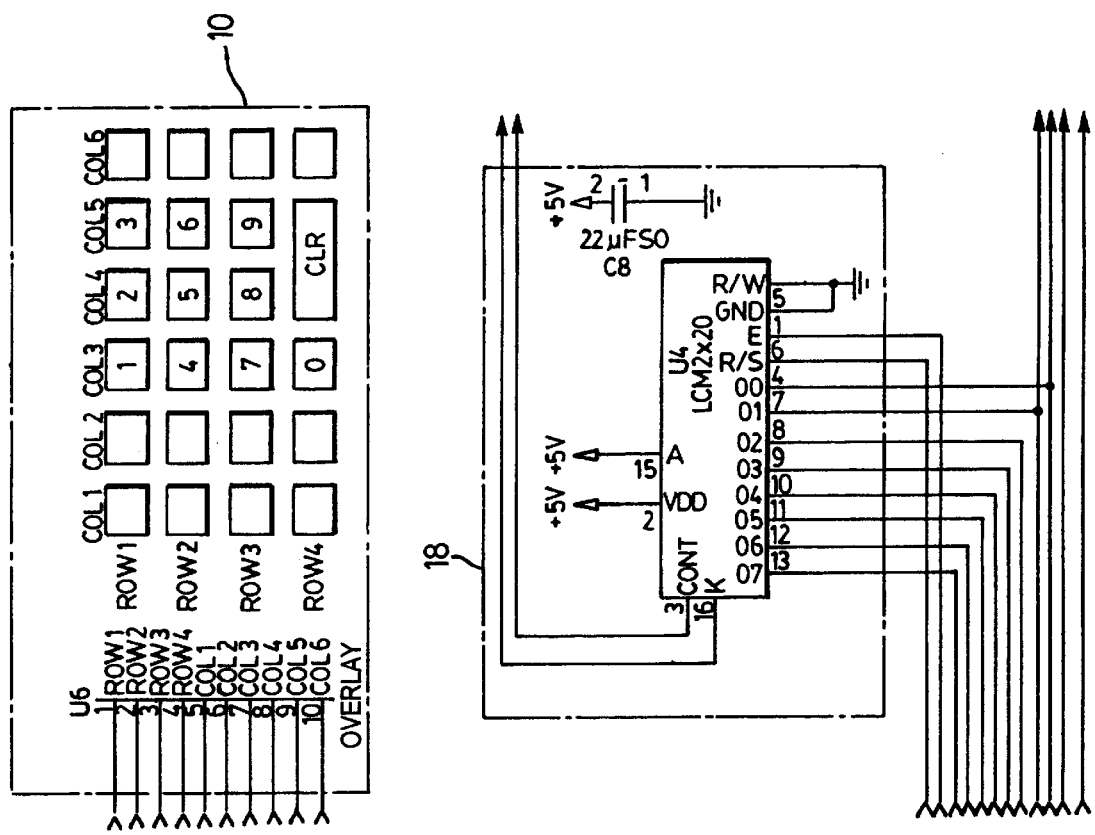
Figures 4, 6:
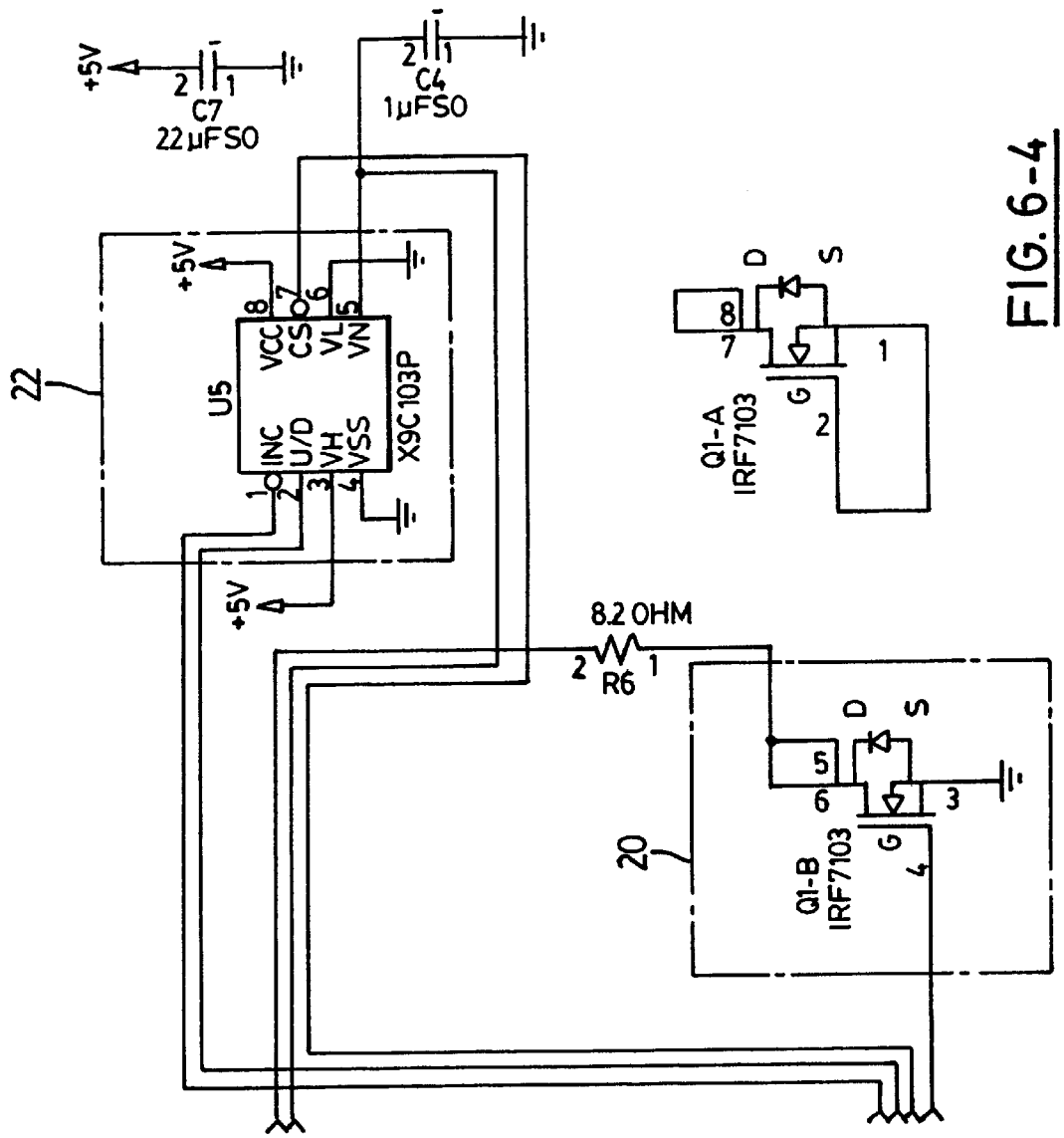

A typical base unit 8 is shown in FIG. 6 as having a keyboard 10 connected to a microcontroller 12 (a single chip) having an EPROM RAM memory 14. Circuit 16 provides the required clock signal. Information entered from the keyboard is decoded and processed by microcontroller 12 and is instantly displayed and updated on a liquid crystal display module 18. The display has a backlight feature which is controlled by the microcontroller via circuit 20. The user can select the on/off state of the liquid crystal display module backlight from the keypad. Circuit 22 is a digital potentiometer which provides contrast adjust by the user keypad via the microcontroller.

The memory 14 is a 10 kilobyte serially interfaced EEPROM memory used to contain the protocol data for up to 1,000 protocols.

Battery level is monitored, and displayed on display module 18 by the microcontroller using R1, R2, C1 as a voltage mirror. The battery charge rate is fixed by R5. Diode D2 eliminates a voltage drop across R5 during normal operation. Diode D1 protects the entire circuit against incorrect polarity on the charger.

Visible or invisible light coming from the probes can be tested by phototransistor Q2. If the incoming light exceeds a preset threshold, set by V1, a display message on the display module 18 indicates that a present light signal exists on the probe unit.

Audio beeper 24 is used to provide acoustical feedback for event confirmation such as keystroke or low battery level. Capacitors C2, C3, and C5 to C8 provide noise decoupling and voltage stabilization for the circuit.

The protocols stored in the base unit shown in FIG. 6 may be transferred to wireless probe units (to be described) using output plug 26.

Wireless Probe Units

Figures 1, 7:
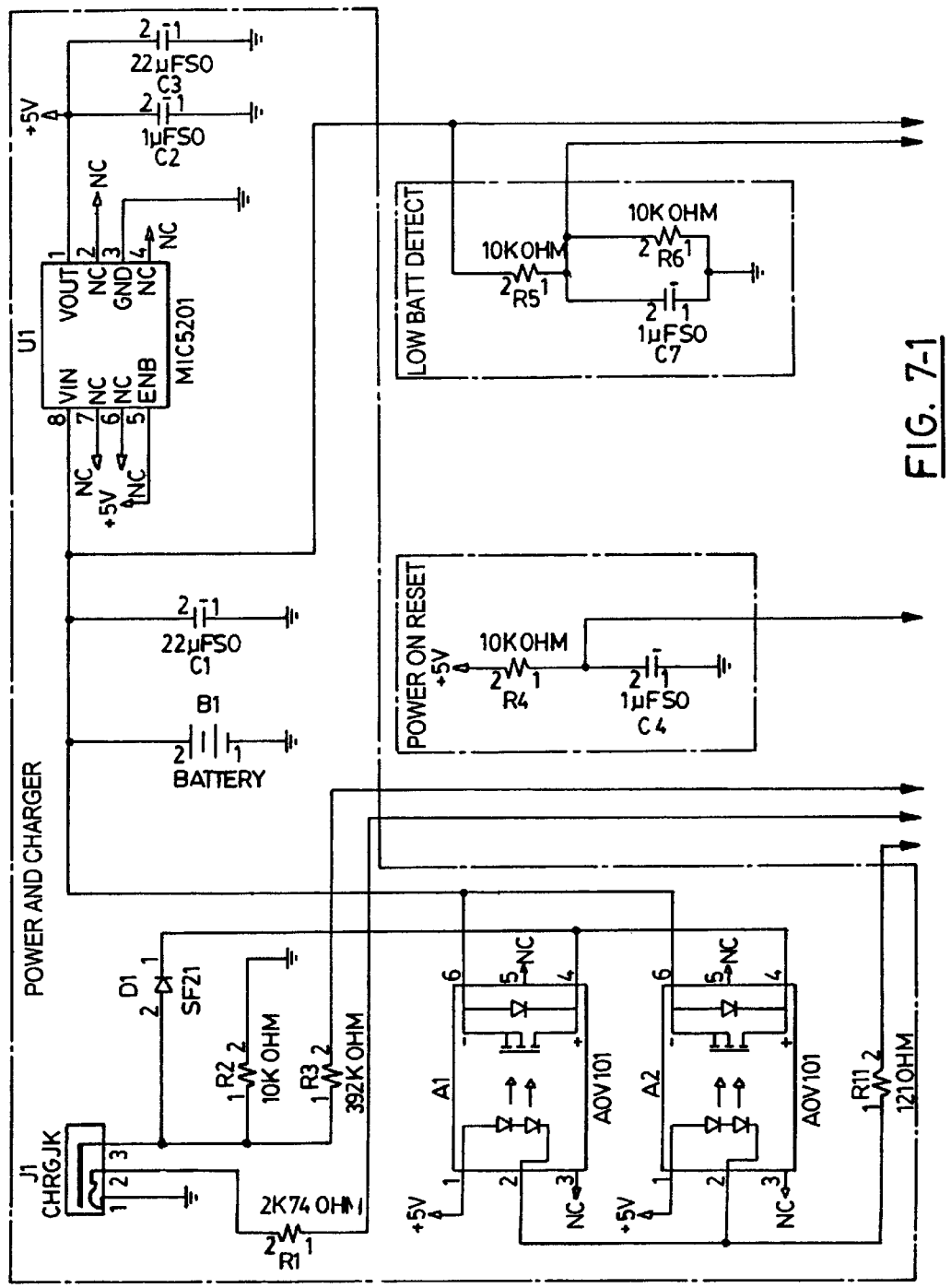
FIG. 7 is a circuit diagram of a probe unit according to the invention.
Figures 2, 7:
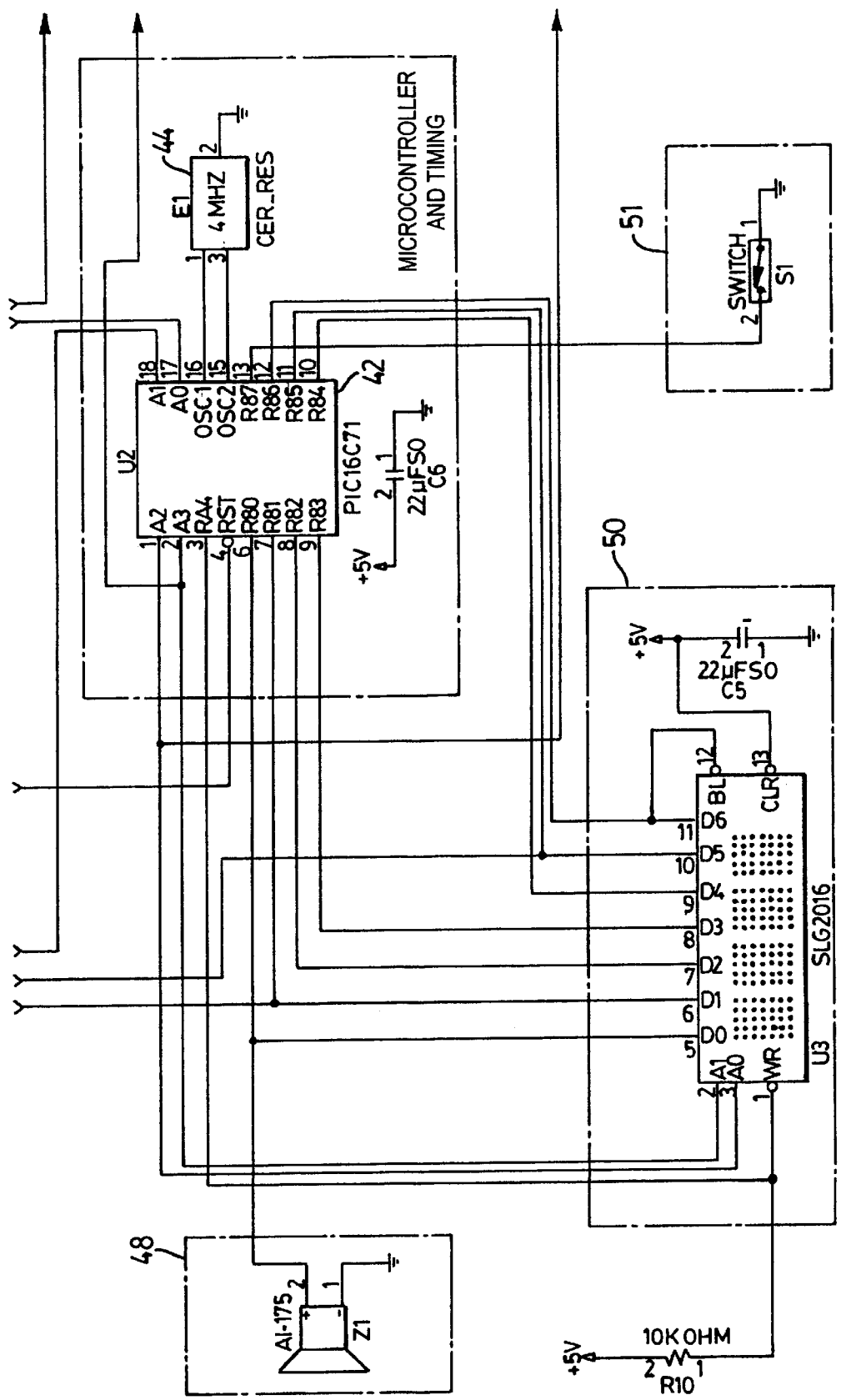
Figures 3, 7:
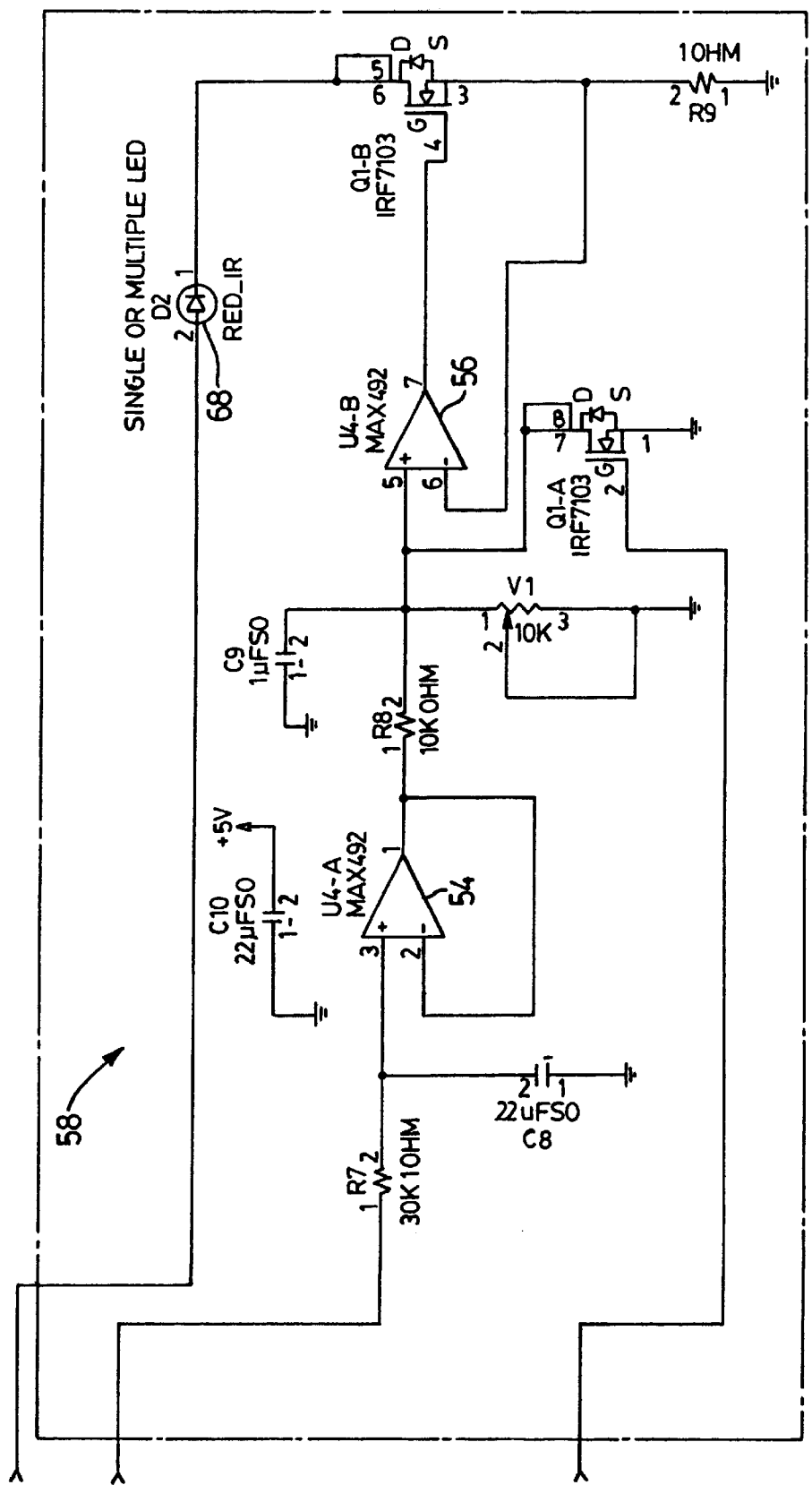

The wireless probe units receive the optical parameter protocols from the base unit and are used to apply LEPT to the patient. A typical wireless probe unit is shown at 40 in FIG. 7 and includes a microcontroller and timing circuit 42 clocked by a 4 MHz ceramic resonator 44. Microcontroller U2 is a single chip with EPROM program memory and suitable RAM. Capacitor C6 provides noise decoupling for the microcontroller.

Battery voltage monitoring and charging is performed once per second by the microcontroller with the help of R5, R6 and C7 as a battery voltage mirror and A1, A2 as power relays to provide connections/disconnections of the batteries to the input charge power. The battery voltage mirror is read by the microcontrollers' built-in analog to digital converter and is translated into battery charge before determining the on/off state of the relays A1, A2.

R4, C4 provide proper power on reset for the microcontroller boot start.

Audio beeper 48 provides an audio indication upon different events such as timer start, timer stop, low battery and the like.

Display 50 is a four digit alpha-numeric LED display which will show system parameters such as timer, power, frequency, unit serial number and the like.

Switch S1 is a momentary single pole, single throw switch used to start or stop the timer or initiate a complete system parameter display.

A software digital to analog pulse width modulated pulse generated on pin 2 of the microcontroller 42 is converted into an analog voltage by R7, C8. This voltage is then buffered by operational amplifier 54. The voltage is then conditioned by adjusting voltage V1 which operates in conjunction with R8 to establish a voltage divider circuit. The resultant voltage is fed to operational amplifier 56 which is part of the transconductance (voltage to current converter) amplifier generally indicated at 58.

Pulses sent to pin 2 of Q1-A by the microcontroller will control the frequency of the signal by switching the output power between on and off modes.

Circuit 60 is a 5 volt voltage regulator which provides power for the total circuit.

Jack 62 acts as a charger connection for the unit (to charge its battery) and also acts as the programming connection, to transfer protocols to the memory of microcontroller chip 42 from pin 26 of the base unit. When a charger is plugged in, the voltage at pin 1 of R3 goes high and informs the microcontroller 42 that the charger is plugged in. If the base unit programmer pin 26 is plugged in instead of the charger, a low voltage on pin 1 of R3 indicates the presence of the base unit programmer connection to jack 62. Diode D1 protects the circuit in the event of an incorrect polarity connection to jack 62.

In use, one central base unit may be used for a clinic, holding all of the required protocols. Individual users may have wireless probe units 40, which they will plug into the base unit 8 (FIG. 6). They will then operate the keyboard on base unit 8 to transfer the required protocols to wireless probe 40 (see FIG. 7), after which they will take the wireless probe unit for treatment. As shown, the wireless probe 40 (FIG. 7) includes single or multiple laser or light emitting diodes 68 which are activated in the required sequence and combinations by the protocols stored in the microcontroller 42 memory.

When a user of a probe unit wishes to change the protocols in the probe unit, he/she simply plugs the wireless unit into the base unit as described and operates the keypad 10 of the base unit 8 to modify or change the protocols which have been stored in the probe unit. Then, when the probe unit is used (by operating switch S1), the lights sources 68 are suitably illuminated under control of the microcontroller and timer 42 to illuminate the area to be treated in accordance with the protocol or protocols stored in the wireless probe 40.

Figure 8:
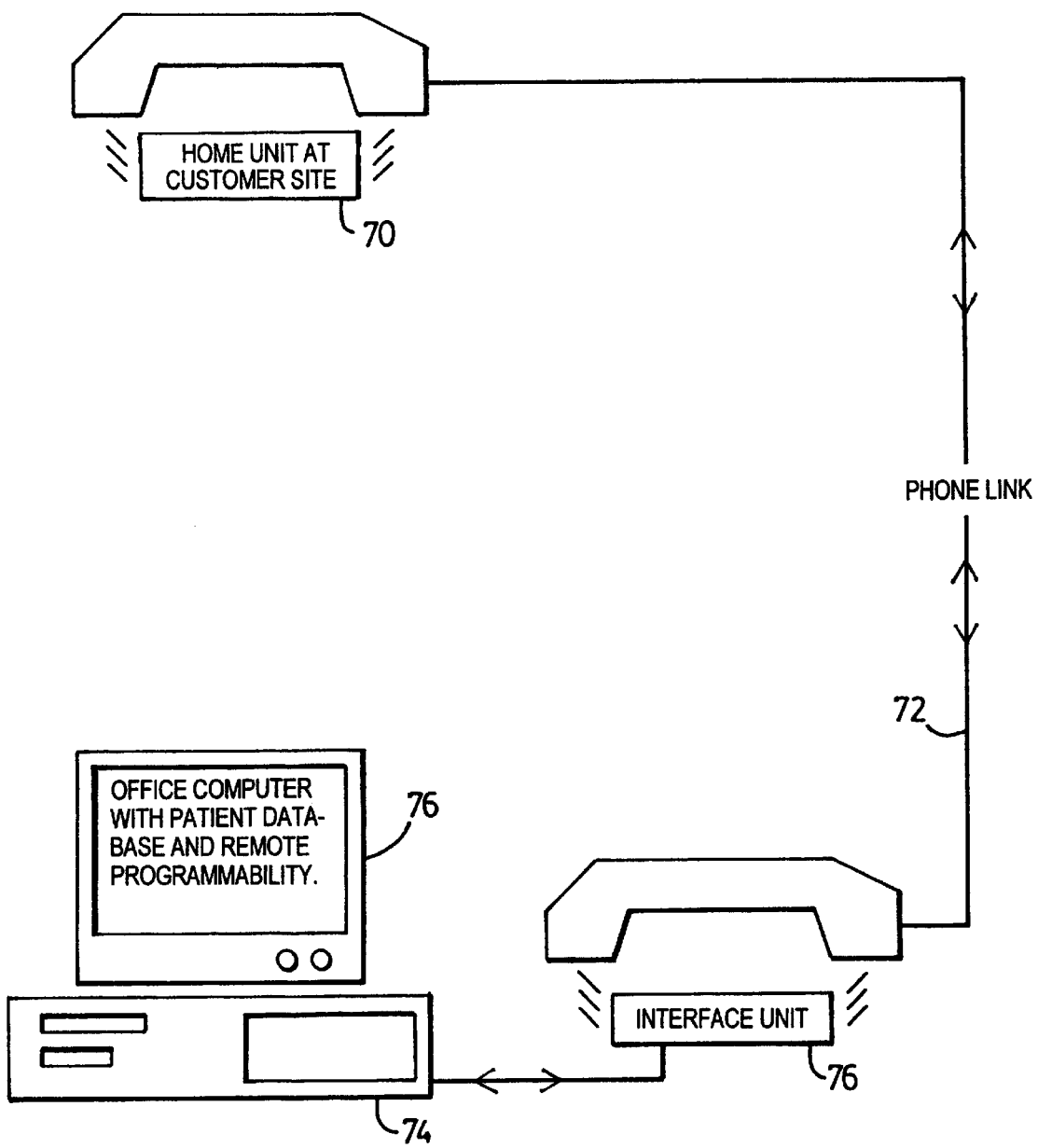
FIG. 8 is a diagrammatic view of a remote probe unit according to the invention.

If desired, and as shown in FIG. 8, the probe unit may be a home unit 70 which includes a modem (not shown) so that it can be programmed remotely by a telephone link 72 (which can include a satellite link), from the base unit 74 which itself operates via an interface unit or modem 76. Thus, customers with the home unit, in their far away locations, can call the location having the base unit and after consulting with a therapist, they can have their home unit programmed for a selected period of operation time and power settings. Alternatively the protocols may be stored in an office computer 76 for transmission to the home unit. The therapist will then enter the desired protocol settings into the computer to be sent to the home unit 70, including the length of time (e.g. one month) during which the home unit 70 is permitted to be operative (all controlled by the microcontroller 42 in the home unit). When the therapist enters a send command to the computer 76, protocol information is transferred to the home unit 70 via the telephone link 72. The remaining time of permitted use, previous protocol numbers and serial number information is sent from the home unit and displayed on the computer, utilizing the home unit microcontroller 42. The therapist can view this information and confirm the home unit's proper time and protocol settings. The computer 76 may be programmed to permit the therapist to keep track of all of the home units and enter his/her comments into the computer as the therapy progresses.

After data is sent by the therapist to the home unit 70 by telephone, the computer 76 may confirm the new data transferred by reading it back to the therapist after the transmission has been completed.

Figure 9:
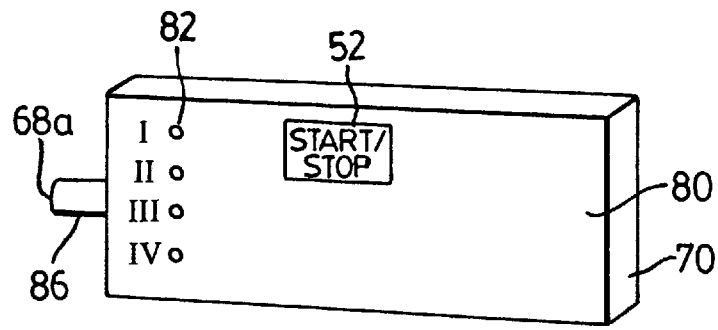
FIG. 9 is a perspective view of a probe unit according to the invention.
Figure 10:
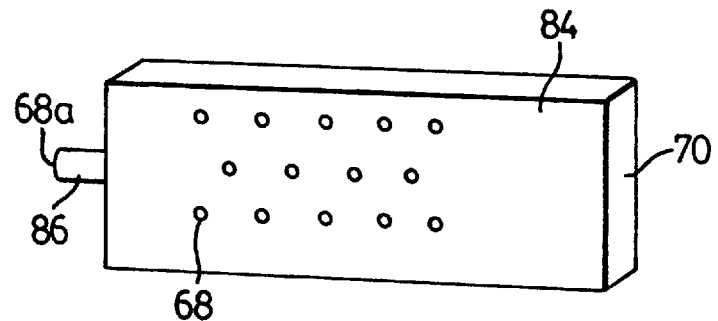
FIG. 10 is a perspective view of the probe unit of FIG. 9 from the opposite side.

Two views of a typical home unit 70 are shown in FIGS. 9 and 10. The home unit 70 is able to store four protocols (all programmable) and its face 80 has four LEDs 82 marked I, II, III and IV, to show which protocol has been selected. A single start/stop button or switch S2 will select the desired protocol, by keeping the switch S2 pressed for more than five seconds to step through the protocols and releasing it on the desired protocol number. The LEDs 82 marked I to IV will light in sequence as switch S2 steps the unit through the various protocols. The switch S2 will also start or stop the treatment by pressing it for less than five seconds and then releasing it. These operations are controlled by the microcontroller 42.

Each or all of the four protocols can be modified as mentioned using a computer and a telephone line, and each protocol can be disabled in the same manner.

The parameters in each protocol include:

Shut down timer: select from one of the following—15 minutes to 30 hours in 15 minute intervals.

Power: Power can be selected from 1 to 12 mW in 3 steps (4 mW, 8 mW, 12 mW) for IR LEDs and 0 to 6 mW in 3 steps (2 mW, 4 mW, 6 mW) for Red LEDs.

Frequency: can be selected from Zero (CW) to 10 Hz in 1 Hz steps and from 10 to 100 in 10 Hz steps.

Modulation Frequency: Can be turned on or off (Modulation freq. e.g.=1.2 Hz).

Point timer: is a count down timer and can be selected from a range of Zero (Manual) to 600 seconds in 5 second intervals.

Probe type selection: Since each unit has a single IR and a multiple (14) red or multiple (14) IR, the selection is included in the protocol.

User Protocol Select Enable/Disable: Home unit can be set to enable or disable the user from selecting the protocols.

User Protocol Selection: Since each unit has 4 programmable (by phone) protocols, the user can select the desired protocol by pressing the start/stop button and scroll through the protocol (when button is released on desired protocol, indicated by one of the 4 LEDs, that protocol will be selected). If any one of the 4 protocols is disabled, it will not light up in the rotation. A maximum of 3 protocols only can be turned off (one protocol must always be enabled).

The other face 84 of the home unit 70 contains 14 light sources (laser diodes) 68 arranged in three rows of five, four and five, so that appropriate patterns of illumination can be provided as required by the protocol selected. A single light source 68a is also provided, located in a stalk 86 extending from the unit so that illumination can be provided using the single source 68a if required by the protocol selected.

Single optical sources are suitable for tender points, trigger points, selected points in the affected area, points on the skin overlying the treatment target (e.g. tendon, spur, calcification deposit), spinal nerve roots, points on the skin overlying selected nerve pathways and other localized (e.g. acupuncture) points.

Multiple optical source (cluster) probes may be used to stimulate affected area (e.g. joint, muscle, ulcer), selected dermatomes, skin overlying selected nerve pathways and reflexogenic zones (e.g. stimulation of the skin overlying carotid sinus with proper optical parameters can reduce elevated blood pressure).

Cluster probes are helpful to reduce treatment time and provide simultaneous three-dimensional treatment. Some LEPT applications are impossible without using cluster probes, because treatment time would otherwise be enormously long (for example, in the case of large ulcers). In addition, even more importantly, cluster probe application can lead in some cases to different physiological body responses compared to point by point stimulation. For example, cluster probe application provides much more pronounced anti-inflammatory and antiedematous effect for acute post-traumatic conditions compared to point by point stimulation. Cluster probe design has to be geared to provide the required three-dimensional light distribution within biotissue to produce the desired physiologic response and therapeutic effect.

Many different types of probes may be used for generating beams of light. If desired the optical source can be a white light source which provides a beam that can be collimated, focussed or defocussed by passing it through a lens and light of particular wavelength may be selected using filters. The beam may be directed to the tissue to be treated through variously shaped bodies with holes to permit passage of the light and to control the pattern of light delivered to the skin. The probe may be shaped to fit the body part to be treated. Examples of suitable probes are shown in FIGS. 11A to 11F, which show a suitable probe having a five by seven matrix of optical diodes 68 illuminated in various patterns as required by the protocol selected.

FIGS. 12A to 12F show an array 90 of optical diodes 68 arranged in a circular pattern. Again, different patterns of LEDs 68 are shown as illuminated, depending on the protocol selected.

Figure 13:
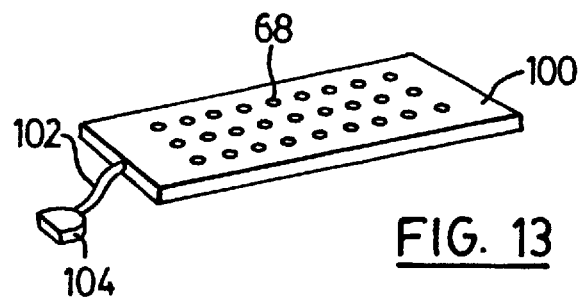
FIG. 13 is a perspective view of a flexible probe unit according to the invention.

If desired, the probe may be constructed of flexible plastic or other suitable material as shown at 100 in FIG. 13, so that it can be wrapped around the surface contours of the body. The probe 100 may be secured in position by adhesive or VELCRO (trade mark) tape as required. Cabling 102 and a plug 104 may be used to plug the flexible part 100 of the probe into the remainder of the probe unit which will contain the circuitry described for selecting and illuminating light sources 68 in the required pattern for the required lengths of time.

Figure 14:
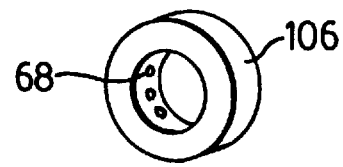
FIG. 14 is a perspective view of a ring probe according to the invention.
Figure 11A:
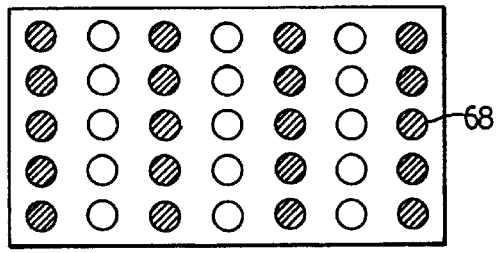
FIG. 11a–f are a diagrammatic view showing various patterns of diodes for use with the invention.
Figure 11B:
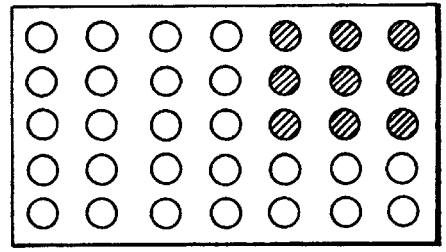
Figure 11C:
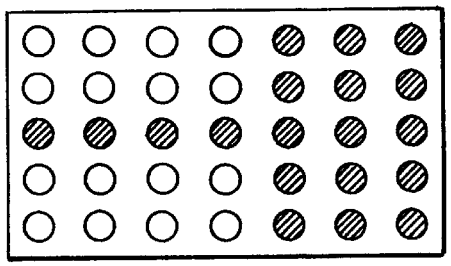
Figure 11D:
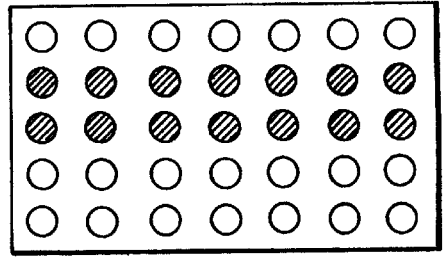
Figure 11E:
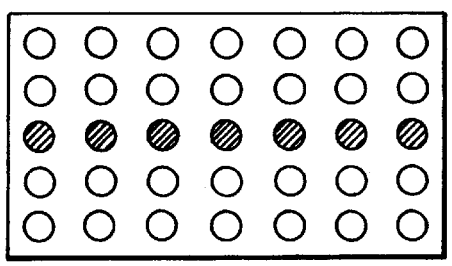
Figure 11F:
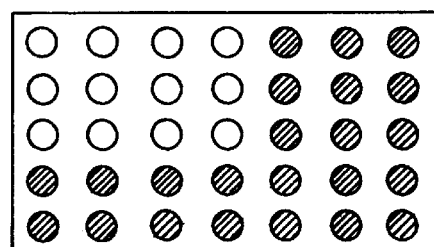
Figure 12A:
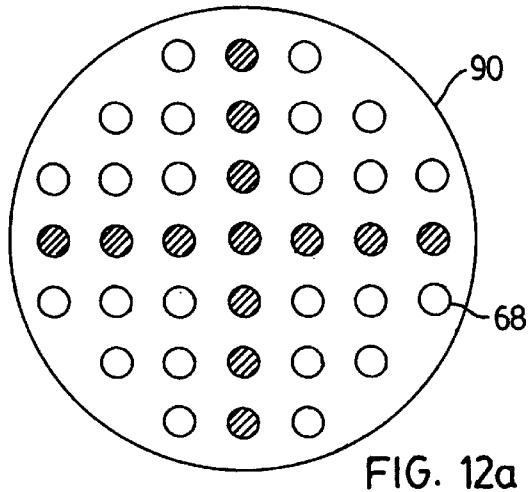
FIG. 12a–f are a schematic view showing alternative patterns of diodes according to the invention.
Figure 12B:
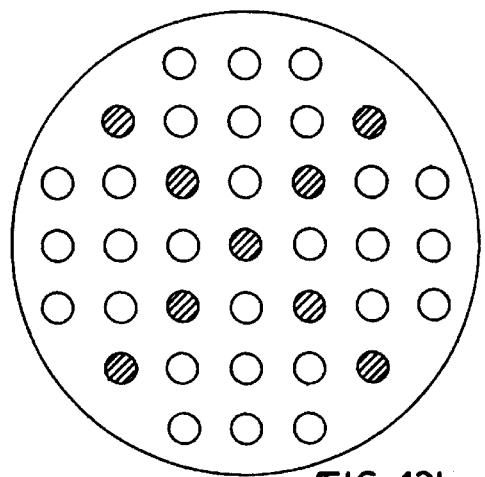
Figure 12C:
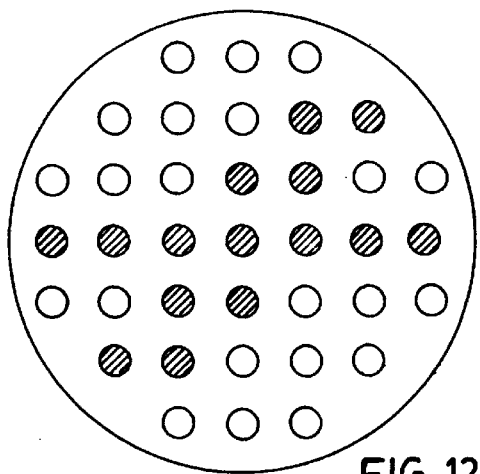
Figure 12D:
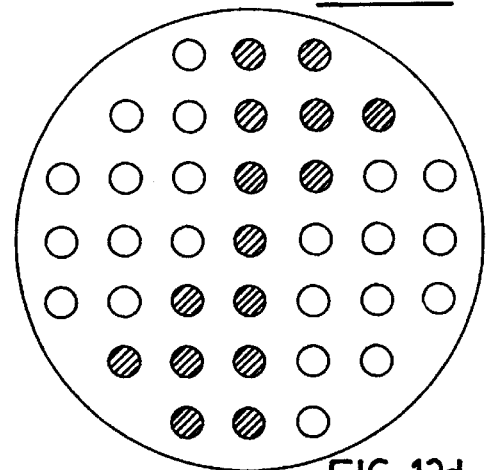
Figure 12E:
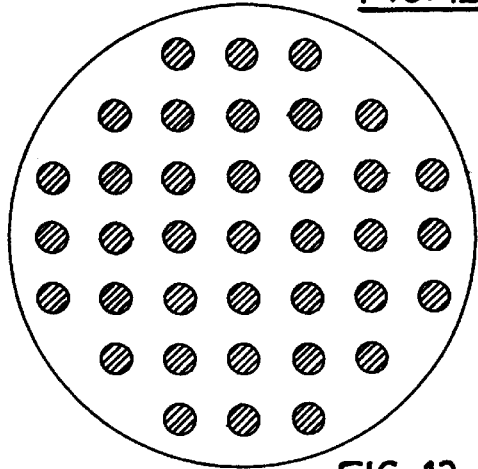
Figure 12F:
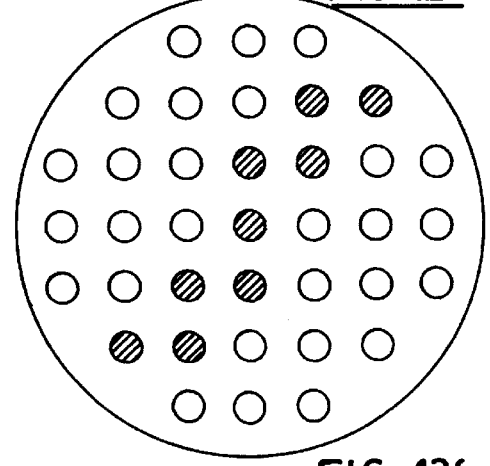

Alternatively, as shown in FIG. 14, a probe unit 106 may be formed in the shape of a ring, having light sources 68 arranged on its inner surface, to apply treatment to a finger. Different size rings may be made for different finger sizes, or an adjustment such as a spring (not shown) may be provided so that the ring will fit different size fingers.

Applying the Beam of Light to the Biological Tissue

There are different LEPT techniques depending on the application. In the contact technique, a probe (single or multiple source) is applied directly to the skin surface. In the contact with pressure technique, a probe is applied to the skin surface with pressure. This technique allows deeper light penetration to the tissue due to the following phenomena: light scattering is significantly less in compressed tissue and light absorption by blood is less because blood is partially squeezed out of the compressed biotissue.

The non-contact technique can be used with both single or multiple source probes. The non-contact technique is used to increase the treated area size. For example, for big size ulcers, the non-contact technique allows to stimulate more ulcer and surrounding tissue surface improving therefore, healing effect; to decrease light intensity on the skin surface and increase simultaneously the treated area size, for example, to induce analgesic effects for tooth extraction specific acupuncture points could be stimulated by He-Ne laser at a distance of about 0.5 m (depending on the beam divergency) for minutes. The contact stimulation by laser with high intensity and short time exposure is not that effective for this purpose.

The scanning technique is used for the treatment of large areas with single or cluster probes. The probe is moved by the therapist or special scanning device along the skin surface with definite speed and the affected area is irradiated by a defocussed laser beam. This technique is used when the laser beam has very small divergence and the area to be treated is large. Defocussing lenses can be used to increase beam size and reduce light intensity. This technique could be used, for example, for the treatment of ulcers and skin dermatosis.

Method for Stimulating Healing of a Disorder

As hereinbefore noted, the present invention provides a method for stimulating healing of a disorder of a biological tissue in a mammal by stimulating the tissue with light having the selected optical parameters as discussed above. Although not wishing to be bound by any particular mode of action, a brief discussion follows of some possible mechanisms of the healing action of LEPT having the selected optical parameters.

At the biomolecular level, LEPT induces changes in the levels of enzymatic activity, including activation of the enzymes of the respiratory chain and of Na, K ATPases. LEPT also induces synthesis of DNA, RNA, ATP and proteins, such as collagen, and alters the levels of cAMP in the cells. At the cellular level, LEPT activates cell metabolism and respiration and secretory activity, such as mast cell degranulation. Cell motility may also be enhanced in motile cells, such as keratinocytes and spermatozoa. Transmembrane transport alterations and cell permeability changes may also result in alterations in intracellular and extracellular ion concentrations. LEPT may also modulate the release of cell cytokines, such as β2 transforming growth factor and platelet derived growth factor.

At the tissue level, LEPT may cause vasodilation, vasoconstriction, anastomosis opening, angiogenesis, blood vessel permeability changes, wound granulation, epithelization activation, skin collagen content and tensile strength increase, increase in mast cell count and degranulation, increase nerve action potential, stimulation of regeneration of damaged nerve tissue and acceleration of bone fracture consolidation.

At the systemic level, LEPT treatment may improve microcirculation in the targeted area, increase lymph flow and lymphatic drainage and result in faster resolution of post traumatic hematoma and edema. LEPT may also exert specific and non-specific effects on the immune system by affecting phagocytosis activation, modulation of reactive oxygen species release by neutrophilic granulocytes, neutrophil chemotaxis enhancement, T-lymphocyte blast transformation, T-Rosette formation activation, killer cell activation and alteration in blood levels of complement and immunoglobulins, including IgA, IgG and IgM. LEPT may also influence the hemopoietic system by increasing the counts of red and white blood cells, including lymphocytes and polymorphonuclear leukocytes and of hemoglobin. LEPT may also exert the following effects: increase in blood protein, alteration in prostaglandin level, decrease in blood viscosity and activation of the blood antioxidant system by influencing levels of catalase, superoxide-dismutase and ceruloplasmin. LEPT may also decrease the erythrocyte sedimentation rate in patients with rheumatoid arthritis. LEPT may further have the following therapeutic effects: antiinflammatory, antiedematous, immunomodulative, microcirculation improvement in precisely targeted areas, soft tissue regeneration acceleration, bone fracture consolidation acceleration and muscle spasm relaxation.

The optical parameter protocols of the treatment may be derived based on the biological tissue or cells size to be treated. The appropriate pulse duration based on the size of the biological structure to be targeted is shown in Table 10.

The method and apparatus of maximal temperature and pressure gradients are generated within biological structures of various sizes by pulsed electromagnetic waves of properly selected wavelength and pulse duration.

To produce an energy gradient within the target biological structure while its electromagnetic wave is propagating through the structure, the following conditions are required:

1. The target biological structure (e.g. vessels, nerve, cell, membrane, mitochondrion, etc.) has to have
   (a) increased electromagnetic wave absorbtion coefficient for definite wavelength (lengths) comparing to the surrounding tissue,
   (b) or decreased specific heat comparing to the surrounding tissue,
   (c) or combination of the conditions a) and b).

Notice: condition a) may be created in target biological structure artificially by introduction of photosensitizer which is selectively bound to this biological structure and has high light absorbtion coefficient for the definite wavelength $\Omega_o$.

2. The maximal energy gradient in the target biological structure of size l and with the maximum light absorbtion coefficient (comparing with surrounding tissue for wavelength $\Omega_o$, will be provided by pulsed electromagnetic wave irradiation with narrow band around wavelength $\Omega_o$ and pulse duration $T_o$ equal to $T_o = l^2/D$ where $D(cm^2/sec)$ is the thermal diffusion constant of surrounding tissue.

The following non-limiting examples are illustrative of the present invention:

EXAMPLES

Example 1

Chronic Leg Ulcers

Fifty patients with infected or non-infected chronic leg ulcers, which had failed to respond to conventional therapy for more than 10 weeks, were treated by LEPT. The chronic leg ulcers were of different etiology and included venous ulcers, diabetic ulcers, decubitus ulcers, burns and post-traumatic ulcers. A combination of protocols 1 and 3 (Table 8) was used for non-infected wounds and a combination of protocols 1 and 2 (Table 8) was used for infected wounds. Following LEPT treatment, 40 of the ulcers (80 %) were completely healed, 5 ulcers (10 %) were reduced in size and 5 ulcers (10 %) were unchanged.

Twenty four patients with 32 infected or non-infected ulcers of various etiology (venous ulcers, diabetic ulcers, decubitus ulcers, post-traumatic ulcers, etc.), which had failed to respond to conventional therapy, were treated by LEPT. Conventional therapy was the same for all three groups of patients and included cleansing with saline, application of wet-to-dry dressing followed by a kling. Total of 15 patients with 18 ulcers were treated with real LEPT, 5 patients with 10 ulcers received placebo LEPT and 4 patients with 4 ulcers received conventional therapy only. Placebo LEPT was provided with the LEPT device looking identical to a real LEPT, however it was producing no output optical parameters. Neither the patient nor the personnel involved in the study were aware of the treatment area the patient was in. This methodology completely satisfied double-blind study requirement. After 10 weeks of treatment the total ulcer size decrease in the real LEPT group was 79.4%, in the placebo group total ulcer size decrease was 31.9% from baseline, and in the control group (conventional therapy only) 45.8% total ulcer size decrease from baseline.

A comparison of the results obtained in the present study with those previously obtained by others using conventional therapy or low energy laser therapy are shown in Table 11, which illustrates the superior results obtained with the LEPT treatment of the present invention.

64 year-old patient, female, presented with the leg ulcer of post-traumatic origin and venous insufficiency. The first onset of the ulcer was 45 years ago after a car accident. The patient had three attempts at skin grafts which had failed. The patient did not allow another surgery. Allergy to antibiotics and to some dressings, severe pain and inflammation developed.

The ulcer's size was 3.9 cm². The patient received LEPT treatments with the following protocol: IR-7-probe, 880 nm, 12 mW, 10 Hz, modulation frequency 1.2 Hz, 25 sec contact on the skin surrounding ulcer and R-22 probe, 660 nm, 6 mw, CW, for 180 s at the distance 7 cm over the ulcer area. After three courses of LEPT (60 treatments total) the ulcer healed completely.

Example 2

Carpal Tunnel Syndrome

Twenty one patients with carpal tunnel syndrome who had been receiving conventional therapy were treated with LEPT three times a week for five weeks. A combination of protocols 8, 19 and 20 (Table 8) was used. Conventional therapy included wrist immobilization at night, specific chiropractic manipulations and vitamins C, E and $B_6$. No corsticosteroid injections during the course of LEPT were applied. Fifteen patients (71.4 %) were free of symptoms and had returned to work after treatment. These patients remained free of symptoms after a 6–18 months of follow up examinations. Two patients (9.5 %) had reduced symptoms and 4 patients (19.1%) did not respond.

A comparison of the results obtained in the present study with those previously obtained by others using conventional therapy or low energy laser therapy are shown in Table 12, which illustrates the superior results obtained with the LEPT treatment of the present invention.

Example 3

Acute Whiplash Injury

Fifty four patients with acute whiplash injury were randomly assigned to three groups. Group 1 (17 patients) received manipulation therapy (MT), Group 2 (18 patients) received MT plus exercise and Group 3 (19 patients) received MT, exercise and LEPT (protocols 6 and 7, Table 8) were administered three times a week for eight weeks. In both protocols 100 Hz frequency and 1.2 Hz modulation frequency were used.

Analysis of variance (ANOVA) was used to test if the patients were properly randomized prior to the study. ANOVA test did not reveal any statistically significant difference between 3 groups in the extensor neck muscle strength (EMS) and uninterrupted sleep (US) at night prior to the study.

The Newman-Keuls' multiple-range test was used to obtain more complete and accurate analysis of data obtained after the course of therapy.

The Newman-Keuls' test revealed statistically significant improvement (SS) in both, EMS and US parameters measured in Group 3 vs. Group 1 and SS improvement in US in Group 3 vs. Group 2. The Newman-Keuls' test did not reveal any SS improvement in US in Group 1 during the course. In Group 2 SS improvement was first observed only after 8 weeks of therapy. In Group 3 SS improvement in EMS was observed much earlier: after 4 weeks of therapy. (See Table 13.)

Example 4

Acute and Chronic Musculoskeletal Conditions

Patients having a range of acute and chronic musculoskeletal conditions were treated by LEPT according to the protocol of the invention as described herein. Most of the patients treated had failed to respond earlier to conventional treatments such as pharmacotherapy and physiotherapy using heat, transcutaneous nerve stimulation, interferential and ultrasound. One hundred ninety nine patients received a course of LEPT. LEPT treatment provided significant improvement of 60–85% of musculosketal conditions.

Eighty five patients with osteoarthritis were treated with LEPT (protocols 8–10, Table 8), of these patients, 59 showed significant improvement and 5 showed some improvement.

Fifty patients with low back pain were treated with LEPT (protocols 8, 11, 13, 24, Table 8), of these patients, 39 were free of symptoms or showed significant improvement and 5 showed some improvement.

Seventy three patients with degenerative disc disease were treated with LEPT (protocols 8, 11, 13, 24, Table 8), of these patients, 44 showed significant improvement.

Thirty two patients with tension headache and neck pain were treated with LEPT (protocols 13, 14, 15, 24, Table 8), of these patients, 24 showed significant improvement and 2 showed some improvement.

Twenty patients with spurs were treated with LEPT (protocol 15, Table 8), of these patients, 17 were free of symptoms.

The results from the above-noted LEPT treatments are summarized in Table 14.

Examples of case histories are provided below.

Female, age 39—Acute left shoulder capsulitis: abduction increased 15° after the first treatment with 60% decrease in pain. Abduction increased to 90° following second treatment. Following three LEPT treatments (protocols 8, 14, 24, Table 8) abduction almost normal, pain minimal and no further treatment required.

Male, age 37—Acute right medial collateral ligament strain: after one LEPT treatment (protocols 4, 5, Table 8) was able to resume playing hockey and following two additional LEPT treatments patient was completely pain free and totally able to resume all normal activity.

Male, age 55 three year old rotator cuff tear, which was aggravated by swimming and golf: Had surgery contemplated and utilized cortisone injections, anti-inflammatory and analgesic medications. Pain free and full range of motion following five LEPT treatments (protocols 8, 9, 11, 24, Table 8).

Male, age 74 developed decreased flexion of right elbow. He stopped playing tennis, could not bring a cup of tea to his lips, or shave his neck. X-rays showed a spur on the proximal tip of the radius. After 24 LEPT treatments (protocols 11, 24, Table 8) and manipulation, X-rays showed a spur of ⅓ the original size. Patient could now raise a cup of tea for drinking, able to shave and returned to playing tennis. Follow-up 18 months examination revealed that the patient was still free of symptoms.

Female, age 31 years with rheumatoid arthritis for 10 years, had generalized stiffness, with aches and pains. She came into the clinic with a walking cane. Forward flexion of her body showed 'finger to floor' was 24", and it took her 15 minutes to climb the subway stairs. After 15 consecutive LEPT treatments (protocols 8, 9, 10, 11, Table 8) and manipulative therapy, she no longer uses the cane, 'finger to floor' is 6" and she is up the subway stairs in 5 minutes.

Female, age 41 with chronic cervical degenerative disc and joint disease along with pain for 15 years. After 15 consecutive LEPT treatments (protocols 6, 7, 11, 24, Table 8), manipulative therapy and specific neck exercises, she no longer experiences pain, has increased motion, sleeps better and smokes 50% fewer cigarettes per day. Modulation frequency 1.2 Hz in CW mode was used in protocols 6 and 7.

Male, age 42 with chronic low back pain and radiation into the left hamstring and popliteal muscles. MIR studies indicated a mild disc bulge at L4–L5. After 8 consecutive LEPT treatments (protocols 13–15, 24, Table 8), manipulative therapy and specific exercises, patient has returned to jogging without pain, radiation or stiffness, and has increased range of movement.

Female, age 71 year complained of severe knee pain with frequent episodes of swelling, causing her to be practically immobile. She was able to trace back her knee problem as having begun at age 51 and could recall only a few periods of remission, lasting no longer than three weeks, after having received steroid injection. Functional inquiry indicated episodes of frequent abdominal pain (very sensitive to weather changes) and back pain which, on their own, she felt she would have been able to tolerate. However, in conjunction with the knee pain, she was not able to tolerate these symptoms. Her past history indicated that she had good health until age 50, it was later found that she has polylithiasis, for which she had not been operated on. She also has a tendency towards constipation and epigastric pain. She suffers from arteriosclerotic heart disease, with stable angina pectoris, and is on multi-pharmacy treatment. In addition, she is constantly taking different types of non-steroid anti-inflammatories. Musculoskeletal examination revealed the presence of moderate varus alignment of the knees, of at least 7–10 degrees. There was moderate joint effusion in the left knee, with significant patellofemoral and medial joint compartment crepitation, on the left more so than on the right. X-ray showed considerable osteoarthritis changes involving both knees.

The patient underwent 12 LEPT treatments (protocols 8, 9, 10, 11, Table 8). During and after treatment, the patient was able to report a decrease in the frequency of her non-steroid anti-inflammatory intake, and said that she had remained free of severe knee pain for the past 1 ½months.

Male, 70 year old complained of right shoulder pain, which had become particularly bothersome over the past few weeks, and which had begun depriving him of adequate sleep. The patient stated that the pain had developed gradually over the last three months, and that it had not been responding to conventional physiotherapeutic treatment modalities, using heat and TNS. Interferential treatment had also failed to improve his condition. The patient was unable to tolerate anti-inflammatory drugs because of gastrointestinal upset. He stated that, using potent analgesics such as Tylenol#3, he was only able to sleep for short periods. The patient mentioned that in the past he had experienced a few similar-type episodes affecting the right shoulder, but that these had always been easily controlled by means of conventional physiotherapy treatment. Examination of ranges of right shoulder movement showed significant decrease. In particular, abduction was approximately 70 degrees, and external rotation, with elbow flexed, was no more than 5 degrees. He had pain and tenderness over the rotator cuff area, with clicks and crepitation on external rotation. X-rays of the cervical spine and left shoulder were not contributory and, in particular, there was no calcification present. The patient was treated as suffering from right rotator cuff tendinitis.

He obtained 10 LEPT treatments (protocols 8, 9, 10, 11, 24, Table 8), and was able to report a significant improvement in his level of pain, as well as an improvement in his sleep pattern, which began developing gradually following the third LEPT treatment.

Female, 47 year old Esthetician, came to the doctor's office complaining of right heel pain, which was particularly bothersome in the mornings when the heel had to support the full pressure of her body weight. The patient stated that this problem had developed gradually over the preceding six to seven months. The patient was diagnosed to be suffering from plantar tendinitis and was treated by means of conventional modalities, such as ultrasound, heat, and steroid injections to the heel, all of which failed to achieve appropriate results. Her past history revealed that she suffers from peptic ulcer disease and is, therefore, unable to tolerate any non-steroid anti-inflammatory medication. Examination showed no neurological deficit present. There was localized pain on the middle of the heel.

The patient reported a significant improvement on her fourth LEPT treatment session (protocols 11, 24, Table 8) and after 10 treatments her pain had disappeared completely.

Male, 43 year old with chronic neck stiffness, decreased range of movement and intermittent radiation into the right biceps. After 15 LEPT treatments (protocols 13–15, 24, Table 8), manipulative therapy and specific neck exercises he has no longer neck stiffness, increased range of movement and no radiation into the right biceps. He also sleeps better.

Female, 43 year old with chronic low back pain and burning sensation in her feet—"feels like I am walking on hot coals". After 10 treatments of LEPT (protocols 13–15, 24, Table 8) and manipulative therapy, she is experiencing a 50% decrease in both her low back pain and the burning sensation in her feet. She reports also that she is walking nearly normally.

Male, 25 year old, diagnosed with bursitis in the sub deltoid bursa for the past year, resulting in decreased range of motion, inflammation and pain. Treatment strategy was implemented and after a full course of LEPT treatments (protocols 4, 11, 24, Table 8), patient retained complete range of motion, experienced no further inflammation or pain.

Example 5

Post-Surgical Complications

More than 100 patients having a range of post-surgical complications, such as swelling, scars, were treated by LEPT according to the protocol of the invention as described herein. LEPT treatment resulted in faster resolution of post-surgical complications, smooth and tender scar formation and improvement of old scar tenderness, elasticity and softness.

Examples of case histories are provided below.

Male, age 47—two previous laminectomies and surgeon hesitant regarding a third: Patient was reduced to a level of an invalid with constant left thigh pain and severe walking limitations. Following ten LEPT treatments (protocols 8–11, 24, Table 8), patient was able to stand normally and walked relatively normally with diminished pain by 60%.

Female, age 24 suffered chronic headaches and dizziness. As a child she had TMJ surgery to control her headaches. After 8 consecutive treatments of LEPT (protocols 22–24, Table 8), manipulative therapy and specific upper cervical exercises, she no longer experiences headaches and dizziness. She sleeps better and has more energy in the day.

Male, surgical face lift which did not take well. There was a tremendous amount of swelling and redness around the neck area of the scar. He has completed 6 LEPT treatments (protocols 4–5, Table 8), and the swelling-has significantly subsided, the redness has disappeared and the scar healing has taken effect, and is hardly noticeable.

Example 6

Acute Trauma and Chronic Post-Traumatic Conditions in the Soft Tissues and Bones One hundred twenty patients having a range of acute trauma and chronic post-traumatic conditions in the soft tissues and bones were treated by LEPT according to the protocol of the invention as described herein. Conditions treated include post-traumatic conditions in muscles, ligaments, joints, bones, etc. such as whiplash, sprains, strains and sport injuries in the foot, ankle, leg, knee, neck, shoulder and elbow. LEPT treatments were administered in accordance with protocols 4, 5 (Table 8) at acute stage followed by protocols 8, 11, 24 (Table 8) for subacute stage of post-traumatic conditions.

Treatment with LEPT resulted in fast resolution of swelling, hematoma, inflammation and pain and accelerated regeneration of injured soft tissue, bone fracture consolidation, soft scar formation, muscle function and general recovery. Examples of case histories are provided below.

Female, multiple injuries, car ran over her. Back sprain, knee swelling. After treating her 2× week with LEPT for a period of 4 weeks, she is 85% recovered. Before starting LEPT MD wanted to operate on knee to remove calcium build-up causing immobility. Now she can walk and has significant movement in knee, the surgery has been put off.

Male, 33 year old with severe lacerations on hand. Extension palmar branch of ulnar nerves damage, patient unable to flex or grip with hand. Before completion of full course of LEPT treatments patient had significant improvement in grip and flex abilities, no pain or inflammation was apparent. Patient discontinued treatment.

Crushed hand injury from job accident. Fracture of the metacarpal bone. Extreme swelling, edema and pain, suggested treatment was to surgical incise hand to alleviate extreme edema and inflammation. LEPT treatment was offered and after first treatment 85% of swelling subsided, pain was almost completely diminished. Patient returned to work the next day. After 3 LEPT treatments condition was under control.

Non-Union of the Tibia—After 21–22 LEPT treatments, re X-ray was performed. No change in bone fusion noted. However, soft tissue was completely healed and pain was substantially reduced.

Gun Shot Wound—A wound inflicted in the web space of hand between thumb and index finger. Conventional therapy failed to improve severe swelling, deep, open wound of ¼ inch, tremendous pain and slight infection. After first LEPT treatment swelling had subsided, inflamed area was greatly reduced and cicatrising had commenced. By 4 LEPT treatment the total wound was closed and normal healing was underway.

Female, age 46—Low back pain injury 2 ½ years ago: in constant pain and specialists contemplating surgery. Patient had difficulty walking, sitting and sleeping. After 8 LEPT treatments pain free and able to engage in normal activity with minimal pain.

Male, 44 years had a history of 3 whiplash injuries 13 years ago. Presently has left cervical pain with radiation into left shoulder and headaches. X-rays showed moderate degeneration of the C5-6 disc with a straight cervical spine. After 15 LEPT treatments and specific exercises, patient has no headaches, no cervical pain or radiation and increased ability to sleep. X-rays showed a return to the normal lordotic cervical curve.

Female, 56 year old who operates a Ballet School, in addition to teaching ballet. She complained of severe back pain, which she had developed suddenly after bending forcefully while still trying to retrieve something from the floor. Over the next few days, her back pain deteriorated further, to the point where she required assistance in order to even dress herself. Analgesic and myorelaxants failed to help her. The patient was desperate to return to work for fear of losing her business. She was advised to immediate LEPT therapy. On examination ten days after the onset of symptoms, she still appeared to be in acute distress, as she required help in order to get up out of the chair and onto the examining table. On examination her range of back movement were significantly reduced, as she was hardly able to reach to the knees on flexion. She had pain and tenderness over the lower paravertebral muscle group. The patient's response to LEPT therapy was immediate, with a gradual improvement in pain level and ranges of back movement after 12 treatments. A two week observation period following treatment, indicated that the patient was free of symptoms.

Male, 41 year old was referred to Toronto Chiropractor Clinic. He had two motor vehicle accidents—"hyperextension whiplash injuries", the last being 12 years ago. At consultation, patient was experiencing neck pain on the left side with low grade radiation into the left biceps. This condition was of permanent nature. Under strenuous activities such as gardening or carrying heavy grocery bags on the side, the radiation would progress to his left hand and index finger. Physical examination revealed normal reflexes and grip strength. The flexor-extensor neck strength ratio was inappropriate, whereby the flexor strength had increased compared to the extensor. X-rays showed that the cervical spine had lost its normal lordotic curve. There was also degenerative changes at C5C6.The course consisted of 15 LEPT treatments to the posterior and left lateral cervical spine, 3× week. A few sessions were missed, so that the total course duration was six weeks. The special exercises were done 5× week at nights before bed. After the course of LEPT and exercises the patient was free of symptoms. Re X-rays showed that the patient's cervical lordosis became close to normal. Follow-up 18 months examination revealed that the patient continued to do exercise and was free of symptoms.

Example 7

Repetitive Strain Injuries

Patients having a range of repetitive strain injuries were treated by LEPT according to the protocol of the invention as described herein.

Male, 43 years old with history of 'carpal tunnel' symptoms for one year. After 4 treatments with the LEPT (protocols 17–20, Table 8) and specific manipulation of the wrist, he no longer suffers with these symptoms.

Male, 66 year old was presented with bilateral wrist pain. He had previously consulted an orthopedic surgeon and was booked for bilateral surgical release of the median nerve for carpal tunnel syndrome. The patient works in a dental lab and is required to perform repeated movements of the wrist and forearm while pinching and grasping small instruments. He first noticed pain in the wrists and thumb while riding his motorcycle. This progressed to pain and numbness while sleeping which awakened him. Relief was achieved by shaking the hands. Finally, he was unable to perform his job adequately as his grip was too weak. The patient was undergoing treatment for low back pain when he informed me of his wrist pain and forthcoming surgery. We discussed LEPT therapy for his carpal tunnel syndrome and treatments began immediately.

The diagnosis was based on patient history, the nerve conduction and EMG studies done by the orthopedic surgeon. In addition, the Phalens test and Tinels sign were positive and reproduced pain along the median nerve. There was bilateral atrophy of thenar eminence. Therapy included LEPT 3× week, vit. C, vit. E, vit. B6 supplementation, also the patient was instructed to wear wrist braces to immobilize the wrists at night. Specific chiropractic manipulation was carried out on dyskinetic joint of the wrists, elbow and neck as required. Soft tissue therapy included trigger point therapy along the forearm wrist flexor muscles and myofascial release, as required. Complete resolution of the symptoms was achieved after 35 LEPT treatments (protocols 17–20, Table 8). The surgery was cancelled and there has been no reoccurrence to date, 15 months following the end of treatment.

Example 8

Neurological and Neuromuscular Conditions

Patients having a range of neurological and neuromuscular conditions were treated by LEPT according to the protocol of the invention as described herein.

Female, 51 year old who works as a medical secretary, complained of the spontaneous onset of numbness and a tingling sensation involving the left hand. Shortly after, these symptoms settled into the inner border of the left forearm, and the fourth and fifth digits of the left hand. Her functional inquiry was unremarkable. Prior to this development she has been in a good health. Objectively, the patient was free of any neurological deficit, and in particular, was found to have no organic pathology present in the distribution of the medial or ulnar nerves. The patient was seen by a orthopedic surgeon and a neurologist, as well as by a rehabilitation medicine specialist, all of whom agreed that there were no objective findings, compatible with nerve degeneration, present. This was substantiated by X-ray examination as well as by EMG studies. All the specialists agreed that the patient was suffering from left ulnar neuropathy. Initially, the patient was treated by means of TNS, analgesics, and vitamins, for a period of four weeks, displaying very little improvement in her symptoms. Ten LEPT treatments (protocols 21–24, Table 8) have proven to be successful, as following the LEPT therapy the patient has been asymptomatic for the last two months.

Example 9

Dermatological Conditions

Patients having a range of dermatological conditions were treated by LEPT according to the protocol of the invention as described herein.

The patient with chronic ulcers were treated in accordance with protocols 1–3, Table 8, depending on the ulcer condition (infected, acute inflammatory condition or non-infected ulceration).

47 year old patient, diabetic-had bilateral toe amputation followed by skin grafting. Skin graft healed slowly and 3 ulcers developed on both feet which did not respond to any conventional therapy. After the first course of 19 LEPT sessions administered for 2 out of 3 ulcers (3× week) 1 ulcer healed and 1 improved. After the second course of 29 LEPT treatments all ulcers healed.

65 year old female presented with 2 ulcers: L tibial ulcer which persisted for 3 years and right distal tibial ulcer which did not heal for 1 year. There were 3 skin grafts attempts over the years and all failed. The patient complained of burning sensation around all ulcers that kept her up at night. After 6 LEPT treatments (3× week) she was able to expose ulcers to air without pain. After 8–10 treatments her night pain was markedly reduced. Her right tibial ulcer healed after 30 sessions of LEPT and left tibial ulcer healed after 48 sessions of LEPT. Six months follow-up the patient is free of ulceration.

73 year old patient, male presented with 35 cm2 ulcer on his big toe and adjacent foot area. The ulcer did not respond to conventional therapy for more than 3 months and was heavily bacteria-contaminated and had a lot of necrotic tissue. LEPT treatments were provided 3× week. After 20 LEPT treatments ulcer decreased in size by 50% and the patient had 2 weeks interval in LEPT. After this interval in LEPT 2 new breakdown areas developed on the same foot. LEPT treatments were resumed on all 3 ulcers, 3× week. After total 42 LEPT treatments all ulcers completely healed. At the 14 months follow-up the patient is still free of ulceration.

60 year old female was admitted to Hospital burn-unit with burns 20 cm2 to the right foot, scalded by hot tea. Burn was infected and did not respond to antibiotic treatment and daily cleaning for 3 weeks. Plastic surgeon intended to do skin grafts, but decided to try LEPT first. The patient was treated daily (5× week). After 14 sessions burns completely healed.

96 year old female with pressure ulcer 3 cm diameter on heel which did not heal for 1 year. Plastic surgeon tried to close the defect but skin graft broke down. Patient was being treated with dressings but they did not help. Patient complained of pain and was taking 3–4 Tylenol #3 daily. Patient received 10 consecutive LEPT treatments. After 10 treatments pain medications reduced to 1–2 Tylenol #1 tablets per day. After 25 treatments (5 weeks) ulcer healed.

Female, 77 year old presented with mixed arteriovenous etiology ulcer on the right foot more than 200 cm2. The ulcer onset happened in 1976 and had been open since then with occasional closing. This ulcer persisted growing in size and became bacteria-contaminated despite different dressings and antibiotics used. The underlying causes of this ulcer was venous insufficiency, ischemia and osteomyelitis. Three previous skin grafts failed. Recently, the patient developed allergy to some dressings. Besides ulcer history, patient had in 1986 hysterectomy followed by radiation therapy after being diagnosed with adenocarcinoma uteri. The course of LEPT started at the end of Sept. '93. The LEFT therapy was provided 2–3× week. The ulcer remained bacteria-free for a few months (~55 treatments) and size decreased by 50% and a bridge of new skin formed on the anterior part of the right foot separated one huge into 2 smaller ulcers. Taking into account the patient's age, nutritional status, failed skin grafts, bacteria contamination of the wound prior our treatment commencement the decrease in size by 50% was a major achievement.

Female, 82 years old had 2 venous stasis ulcers for about 2 months prior to receiving LEPT. During this period, nurses were visiting her for about 3× week for dressing changes with the wound showing little or no healing. Nursing visits were reduced after starting LEPT, although continued to monitor other health problems. The wounds (the largest approximately 1.5 cm in diameter) after initiating LEPT were healed following 27 sessions over 9 weeks. The staff also noted improved color in the affected limb after only a few treatments. The lady also had cellulitis, dementia and anemia. Although this case was difficult with other aspects of home-care, the compliance with LEPT treatments was total.

57 year old diabetic patient had a 2 cm in diameter ulcer on the metatarsal head of his left foot. He had a history of ulcers over a period of 10 years with his diabetes. In late November he was admitted to DECH with cellulitis and received surgical debridement of this current ulcer. EMII nurses began following him in mid December for IV therapy and dressing changes, with the wound showing only limited or no healing by mid March. He also had peripheral neuropathy, hypertension and nephropathy. After 30 LEPT treatments, this wound had closed. Nurses originally were visiting 3× week diminishing to only 1× week as IV therapy discontinued and patient was managing own dressing changes at the time LEPT started. These visits were discontinued shortly after as the physiotherapist carried out the care required.

Female, 58 years old with Multiple Sclerosis had two wounds (2 cm and 1 cm in diameter) in her coccygeal region for over two years. The wounds showed little success in healing. Nurses had been visiting 2–3× week since mid Nov. '93 but this had decreased to 1× week in Feb. '93. The lady was paraplegic with decreased sensation in her lower limbs. The wounds were due to friction resulting from inefficient transfers. 28 LEPT treatments were given over a 9 ½ week period, resulting in closure of both wounds.

A 48 year old female had been suffering from herpes simplex attacks on her lips, for 30 years. These attacks were especially frequent in a cold time of year and under stressful conditions. Painful herpes simplex lesions did not respond to any conventional therapy and usually it took from 9 to 15 days for a lesion to get healed. Low Energy Photon Therapy with a dose $8J/cm^2$ and a wavelength of 660 nm was used to treat the lesion locally. The patient experienced immediate pain relief and lesion became dry within 1–2 days after the first treatment. One to three LEPT treatments were enough to reduce lesion healing time to 3 to 6 days. The next lesion never appeared again at the spot previously treated by LEPT. The patient successfully used a home LEPT unit to treat herpes simplex lesion early on the lesion onset and to prevent lesion development as well during one year. For three years follow-up after the last LEPT course the patient did not have any herpes simplex attacks.

Tables 11, 12, 13 and 14 which follow show comparative analysis of LEPT versus conventional therapy for skin ulcers, carpal tunnel syndrome, and acute whiplash injury respectively, as well as a summary of LEPT results which have been achieved to date. In addition, the information given in the appended claims is hereby incorporated into the disclosure.

TABLE 11

Comparative analysis of LEPT/LLLT/conventional therapy efficacy for skin ulcers

Efficacy of ulcer healing

| Condition | LEPT (IMI Inc.) product | LLLT | Conventional Therapy |
|---|---|---|---|
| Infected & non-infected venous leg ulcers | 86% at SGH, Toronto<br>Note:<br>86% out of 22 chronic ulcers which didn't respond to CT healed after the course of LEPT (9 week average)[1]<br>93% at EMH, Fredericton<br>SS $p < 0.001$<br>Note:<br>11 ulcers out of 18 healed completely and 7 ulcers improved significantly (79.4% average ulcer size decrease) after 10 weeks in real LEPT treatment group, in placebo LEPT group only 31.9% of total ulcer area decrease was observed; none of the ulcers healed completely. | No SS difference<br>Note:<br>46 pts. were treated in two groups by real & placebo LLLT (for 12 weeks)[2].<br>No SS difference<br>Note:<br>42 pts. Were treated with real vs. placebo LLLT (for 12 weeks)[3].<br>No SS difference<br>Note:<br>12 chronic leg ulcers were treated with real vs. placebo LLLT, total of 20 treatments[4]. | 33.3%<br>Note:<br>Conventional therapy included cleansing with saline, application of paste bandage, followed by a support bandage plus exercise program - only 3 out of 9 ulcers healed after 12 weeks of $CT^2$. |

Legend:
LLLT - low energy laser therapy; LEPT - low energy photon therapy; CT - conventional therapy; SGH - Scarborough General Hospital; EMH - Extra-Mural Hospital; SS - statistical significance; pts. - patients
References:
[1]J. Telfer, Trial on Laser Therapy for leg ulcers. Scarborough General Hospital MedNews, Vol. 6, No. 2, p. 17, 1993.
[2]T. Lundeberg, and M. Malm, Low-power HeNe Laser Treatment of Venous Leg Ulcers, Annals of Plastic Surgery, Vol. 27, No. 6, pp. 337–9, 1991.
[3]M. Malin, and T. Lundeberg, Effect of Low-Power Gallium-Arsenide Laser on Healing of Venous Ulcers, Scand. J. Plast. Reconstr. Surg., Vol. 25, pp. 249–251, 1991.
[4]P. P. Gogia and R. R. Marquez, Effects of HeNe Laser on Wound Healing, Ostomy/Wound Management, Vol. 38, No. 6, p. 38–41, 1992.

TABLE 12

Comparative analysis of LEPT/LLLT/conventional therapy efficacy for carpal tunnel syndrome Efficacy of CTS healing

| Condition | LEPT | LLLT | Conventional Therapy |
|---|---|---|---|
| Carpal tunnel syndrome (CTS) | 15 patients free of symptoms & returned to work (71.4%)<br>2 reduction of symptoms (9.5%)<br>These patients remained free of symptoms after 6–18 months follow-up.<br>Note:<br>21 patients with CTS received LEPT (3 × week, 15 Rx total). | 76.1% (by 60–80% limited) pain reduction only<br>Only 36.5% had limited (by 60–80%) pain reduction after 6 months[1].<br>62% return to work<br>note:<br>160 pts. were given 8 points conservative treatment program plus real or placebo LLLT (3 × week, | 11–40% of patients remained free of symptoms in 6–18 months follow-up after the course of therapy.<br>Note:wrist immobilization with splint, nonsteroid anti-inflammatory drugs, corticosteroid injections into the carpal tunnel[3,4,5] |

TABLE 12-continued

Comparative analysis of LEPT/LLLT/conventional therapy efficacy for carpal tunnel syndrome Efficacy of CTS healing

| Condition | LEPT | LLLT | Conventional Therapy |
|---|---|---|---|
| | | 15 Rx total). The difference in terms of return to work was statistically significant (62% vs. 38%) in real vs. placebo LLLT. There were no mention of follow-up[2]. | |

Legend:
LLLT - low energy laser therapy; LEPT - low energy photon therapy; CTS - carpal tunnel syndrome; CT - conventional therapy; pts. - patients
References:
[1]R. Storaci, F. Prato, La Laser-terapia Nella Syndrome del Tunnel Carpale, Laser & Technology, Vol. 3, No. 1–2, pp. 36–39, 1993.
[2]F. Chadwick, C. Smith, T. Vangsness, T. Anderson, W. Good, Treatment of Repetitive Use Carpal Tunnel Syndrome, An International Symposium on Biomedical Optics, 4–10 Feb., San Jose, USA, Technical Abstracts, p. 194.
[3]Goodman, H. V., Foster J. B., Effect of local corticosteroid injection on median nerve conduction in carpal tunnel syndrome, Ann. Phys. Med., Vol. 6, pp. 287, 1962 (ref. 16 from R. Szabo).
[4]Gelberman R. H., Aronson D., Weisman M. H., Carpal tunnel syndrome: Results of a prospective trial of steroid injection and splinting, J. Bone Joint Surg., Vol. 62A, p. 1181, 1980, (ref. 15 from R. Szabo).
[5]S. J. Kaplan, S. Z. Glicke, and R. G. Eaton, Predictive Factors in the Nonsurgical Treatment of Carpal Tunnel Syndrome, J. Of Hand Surgery, (British Volume, 1990), Vo. 15B, pp. 106–108.

TABLE 13

Comparative analysis of LEPT Manipulative Therapy/Exercise program efficacy for acute whiplash injury Efficacy of LEPT in combined therapy for whiplash injury*

| Condition | MT + Ex + LEPT | MT + Ex | MF |
|---|---|---|---|
| Acute whiplash injury | EMS (neck extensor muscle strength) 23% improvement ss p < 0.05 | EMS 15% improvement | EMS 9% improvement |
| | US (uninterrupted sleep) 37% improvement ss p < 0.01 | US 22% improvement | US 10% improvement | ss - statistically significant
*54 patients with acute whiplash injury were randomly assigned to the following 3 groups:
17 patients received manipulation therapy (MT)
18 patients received MT plus exercises (Ex)
19 patients received MT + Ex + Low Energy Photon Therapy (LEPT)
Therapy was administered 3 × week for 8 weeks.

TABLE 14

| Clinical Entity | # of Cases | SI | I | MI | No Effect |
|---|---|---|---|---|---|
| Osteoarthritis | 54 | 15 (28%) | 22 (41%) | 9 (16%) | 8 (15%) |
| Soft tissue pathological conditions | 69 | 24 (35%) | 23 (33%) | 16 (23%) | 6 (9%) |
| Degenerative disc disease | 62 | 20 (32%) | 17 (27%) | 14 (23%) | 11 (18%) |
| Neuromuscular conditions | 14 | 3 (21%) | 5 (36%) | 4 (29%) | 2 (14%) |
| Total | 199 | 62 (31%) | 67 (34%) | 43 (22%) | 27 (13%) |

Legend:
SI - significant improvement
I - improvement
MI - marginal improvement

While preferred embodiments of the invention have been described, it will be appreciated that various changes may be made within the scope and spirit of the invention.

We claim:
1. An apparatus for treating dermatological, musculoskeletal, soft tissue or neurological disorders of a biological tissue with non-ionizing low energy light having selected optical parameters, comprising:
   (a) a power source for providing power to a central microprocessor;
   (b) a central microprocessor having stored optical parameter protocols suitable for treating a range of said disorders of biological tissue and means for selecting one or more stored optical parameter protocols for the disorder to be treated, said parameters including wavelength, power, intensity and dose;
   (c) an optical probe, having a microprocessor in communication with the central microprocessor, to receive the selected optical parameter protocol, said probe containing an optical parameter protocol, said probe containing an optical source for generating a beam of light having the selected optical parameter protocol and for directing the beam of light to the biological tissue to be treated;
   (d) said optical source including an array of light emitting sources, all of said sources when activated producing substantially monochromatic non-ionizing light having a selected wavelength in the range of from 630 to 2000 nm and a bandwidth not exceeding substantially 30 to 40 nm, and each of said sources providing light of the same said selected wavelength and no other wavelength, (e) said optical source further including a control circuit for activating selected ones of said light emitting sources to produce a three dimensional light distribution at said tissue;

(f) said protocols including a protocol for providing said beam of light as said substantially monochromatic non-ionizing light to stimulate said tissue;

(g) communication means for transmitting the optical parameter protocol from the central microprocessor to said at least one probe; and (h) said probe containing said protocol only for said selected wavelength and not containing any protocol for any other wavelength.

2. The apparatus of claim 1 wherein the beam of light has a wavelength in the range of from 630 to 700 nm, from 740 to 760 nm, or from 800 to 1,100 nm.

3. The apparatus of claim 1 wherein the optical source is a laser, laser diode, light emitting or superluminous diode, which provides substantially monochromatic light.

4. The apparatus of claim 3 including means for operating the optical source in pulsed mode with a pulse repetition rate in a range of from 0 to 200 Hz.

5. The apparatus of claim 1 wherein the optical parameters are selected from the group comprising dose, intensity, frequency, pulse duration, wavelength, power, monochromaticity, intensity modulation with specific endogenous frequencies, three-dimensional photon distribution.

6. The apparatus of claim 1 wherein the communication means are wireless.

7. The apparatus of claim 6 including a plurality of probes for said central microprocessor, each probe being capable, independently of the remaining probes, of receiving one or more optical parameter protocols from said central microprocessor.

8. The apparatus of claim 1 wherein said communication means includes a telephone link.

9. The apparatus of claim 1 further comprising means for monitoring the condition of the mammal and providing feedback to the central microprocessor to adjust the selected optical parameter protocol including adjustment of the phase of stimulation in respect to the endogenous rhythm phase based on the condition of the mammal.

10. The apparatus of claim 9 wherein the means for monitoring the condition of the mammal is on-line EEG, EMG, ECG, a respirator, or chemoluminescence.

11. The apparatus of claim 1 wherein said light emitting sources are arranged in a square or rectangular pattern, to provide said three dimensional photon distribution in the affected area.

12. The apparatus of claim 1 wherein said light emitting sources are arranged in a circular pattern.

13. The apparatus of claim 12 wherein said circular pattern provides photons in an area $(R+1)^2/R^2$, where R is the radius of an affected area of said biological tissue.

14. The apparatus of claim 1 wherein said optical probe includes two sets of light emitting sources, one set comprising a single light source arranged on a stalk, and the other comprising a matrix of light emitting sources arranged on a face of said optical probe.

15. The apparatus of claim 1 wherein said optical probe includes a flexible body capable of adapting to the contours of a portion of a patient to be treated, and a plurality of said light emitting sources arranged on said flexible body.

16. The apparatus of claim 1 wherein said optical probe includes a body arranged in a circular configuration and adapted to fit on the finger of a patient, said body having an inner surface, and a plurality of light emitting sources arranged on said inner surface.

17. The apparatus of claim 1 wherein said probe contains an optical parameter protocol such that said probe provides a dose of from 0.05 to 10 $J/cm^2$, an intensity of from 0.2 to 100 $mW/cm^2$, a wavelength of from 630 to 2,000 nm, a continuous wave mode or a pulse repetition rate of from 0 to 200 Hz, and optional modulation frequencies of said continuous wave mode or of said pulse repetition rate of any of from 0.2 to 0.3 Hz, 1 to 1.2 Hz, and 1 to 5 Hz.

18. The apparatus of claim 17 wherein said probe contains an optical parameter protocol such that said probe provides a dose of from 0.05 to 0.2 $J/cm^2$, a wavelength of from 630 to 700 nm, a continuous wave mode or pulse repetition rate of from 0 to 200 Hz, and optional modulation frequencies of said continuous wave mode or of said pulse repetition rate of any of from 0.2 to 0.3 Hz, 1 to 1.2 Hz, and 1 to 5 Hz.

19. The apparatus of claim 17 wherein said probe contains an optical parameter protocol such that said probe provides a dose of from 2.0 to 5.0 $J/cm^2$, a wavelength of from 630 to 700 nm, a continuous wave mode or pulse repetition rate of from 0 to 200 Hz, and optional modulation frequencies of said continuous wave mode or of said pulse repetition rate of any of from 0.2 to 0.3 Hz, 1 to 1.2 Hz, and 1 to 5 Hz.

20. The apparatus of claim 17 wherein said probe contains an optical parameter protocol such that said probe provides a dose of from 0.1 to 9.0 $J/cm^2$, an intensity of from 300 to 600 $mW/cm^2$ and a wave length of from 800 to 1,100 nm in a continuous wave (CW) mode or pulse repetition rate of 10 Hz or from 50 to 200 Hz, and optical modulation frequencies of said continuous wave mode or of said pulse repetition rate of any of 0.3 and/or 1.2 Hz.

21. The apparatus of claim 17 wherein said probe contains an optical parameter protocol such that said probe provides a dose of from 2 to 5 $J/cm^2$, an intensity of from 10 to 30 $mW/cm^2$ and a wavelength of from 630 to 700 nm.

22. The apparatus of claim 17 wherein said probe contains an optical parameter protocol such that said probe provides a dose of from 3 to 7 $J/cm^2$ or 4 to 25 $J/cm^2$, an intensity of from 10 to 40 $mW/cm^2$ to 60 to 100 $mW/cm^2$ or 300–600 $mW/cm^2$ or 1000 to 5000 $mW/cm^2$ and a wavelength of from 800 to 1100 nm.

23. The apparatus of claim 17 wherein said probe contains an optical parameter protocol such that said probe provides a dose of from 4 to 9 $J/cm^2$, an intensity of from 20 to 60 $mW/cm^2$ and a wavelength of from 630 to 700 nm.

24. The apparatus of claim 1 wherein said probe contains an optical parameter protocol such that said probe provides a dose of from 3.0 to 9.0 $J/cm^2$, an intensity of from 50.0 to 80 $mW/cm^2$ and a wavelength of from 630 to 700 nm, a continuous wave mode or pulse repetition rate of from 0 to 200 Hz, and optical modulation frequencies of said continuous wave mode or of said pulse repetition rate of any of from 0.2 to 0.3 Hz, to 1.2 Hz, and 1 to 5 Hz.

25. The apparatus of claim 1 wherein said control circuit includes a circuit for activating said light emitting sources with a selected pulse repetition rate.

26. The apparatus of claim 1 wherein said optical parameter protocol in said probe is selected according to the color of skin of the patient to be treated.

* * * * *